(12) United States Patent  
Horii et al.

(10) Patent No.: US 9,752,989 B2  
(45) Date of Patent: Sep. 5, 2017

(54) SAMPLE ANALYZING METHOD USING SAMPLE ANALYSIS CARTRIDGE, SAMPLE ANALYSIS CARTRIDGE, AND SAMPLE ANALYZER

(71) Applicant: SYSMEX CORPORATION, Kobe-shi, Hyogo (JP)

(72) Inventors: Kazuyoshi Horii, Kobe (JP); Tomoyuki Nose, Kobe (JP); Tatsuya Kosako, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 45 days.

(21) Appl. No.: 15/082,337

(22) Filed: Mar. 28, 2016

(65) Prior Publication Data

US 2016/0320307 A1 Nov. 3, 2016

(30) Foreign Application Priority Data

Apr. 30, 2015 (JP) .................................. 2015-093515

(51) Int. Cl.
 *G01N 21/75* (2006.01)
 *B03C 1/02* (2006.01)
 (Continued)

(52) U.S. Cl.
 CPC ............ *G01N 21/75* (2013.01); *B01L 3/5023* (2013.01); *B01L 3/50273* (2013.01);
 (Continued)

(58) Field of Classification Search
 CPC ....... B01L 2400/043; B01L 2200/0668; B01L 2200/10; B01L 2300/087;
 (Continued)

(56) References Cited

U.S. PATENT DOCUMENTS 8,158,008 B2 4/2012 Su et al.
8,951,417 B2* 2/2015 Strohmeier ....... B01L 3/502761
 210/695
(Continued)

FOREIGN PATENT DOCUMENTS

JP 2009-148735 A 7/2009
WO 2011/045436 A1 4/2011
WO 2012/041809 A1 4/2012

*Primary Examiner* — Jennifer Wecker
(74) *Attorney, Agent, or Firm* — Mots Law, PLLC

(57) ABSTRACT

A sample analyzing method for suppressing an adverse effect on detection accuracy of a detection target substance is disclosed. In the sample analyzing method, a magnetic particle as a support of a detection target substance is transported by magnetic force to a second liquid container through a passage between a first liquid container storing a first liquid containing the magnetic particle and the second liquid container storing a second liquid containing a labeled substance to form a complex with the detection target substance and the magnetic particle. The complex formed in the second liquid container and containing the detection target substance, magnetic particle, and labeled substance is transported to a third liquid in a flow path, and the magnetic particle is transported to a detection tank for detecting the detection target substance, while being agitated in a mixed liquid of the complex and third liquid within the flow path.

20 Claims, 23 Drawing Sheets

(51) Int. Cl.
*G01N 33/53* (2006.01)
*B01L 3/00* (2006.01)
*B81B 1/00* (2006.01)
*G01N 35/00* (2006.01)
*G01N 33/543* (2006.01)

(52) U.S. Cl.
CPC .......... *B01L 3/502761* (2013.01); *B03C 1/02* (2013.01); *G01N 33/54326* (2013.01); *B01L 2200/0668* (2013.01); *B01L 2200/10* (2013.01); *B01L 2300/087* (2013.01); *B01L 2400/043* (2013.01); *B01L 2400/0406* (2013.01); *B01L 2400/0409* (2013.01); *B81B 1/00* (2013.01); *G01N 33/54333* (2013.01); *G01N 35/00069* (2013.01); *Y10T 436/111666* (2015.01); *Y10T 436/25375* (2015.01)

(58) Field of Classification Search
CPC ..... B01L 2400/0406; B01L 2400/0409; B01L 3/5023; B01L 3/502761; B03C 1/02; B81B 1/00; G01N 33/54326; G01N 33/54333

See application file for complete search history.

(56) References Cited

U.S. PATENT DOCUMENTS

| | | |
|---|---|---|
| 2008/0031787 A1 | 2/2008 | Yu |
| 2009/0227044 A1* | 9/2009 | Dosev .............. G01N 33/54333 436/526 |
| 2012/0035084 A1* | 2/2012 | Su .................... B01L 3/502761 506/39 |
| 2015/0093815 A1 | 4/2015 | Kiani et al. |

* cited by examiner

SAMPLE ANALYZING METHOD USING SAMPLE ANALYSIS CARTRIDGE, SAMPLE ANALYSIS CARTRIDGE, AND SAMPLE ANALYZER

CROSS REFERENCE TO RELATED APPLICATIONS

This application claims priority based on 35 USC 119 from prior Japanese Patent Application No. 2015-093515 filed on Apr. 30, 2015, entitled "SAMPLE ANALYZING METHOD USING SAMPLE ANALYSIS CARTRIDGE, SAMPLE ANALYSIS CARTRIDGE, AND SAMPLE ANALYZER", the entire contents of which are hereby incorporated by reference.

BACKGROUND

The disclosure relates to a sample analyzing method using a sample analysis cartridge, the sample analysis cartridge, and a sample analyzer.

The U.S. Pat. No. 8,158,008 (Patent Document 1) discloses that magnetic particles coupled to a detection target substance contained in a sample are transported by magnetic force from one container to another container in a fluidic system. The magnetic particles coupled to the detection target substance are transported by magnetic force of an electromagnetic coil to a detection tank where to detect the detection target substance from the container into which the detection target substance is injected.

SUMMARY

An embodiment provides a sample analyzing method using a sample analysis cartridge inserted into a sample analyzer that detects a detection target substance contained in a sample includes: transporting a magnetic particle supporting the detection target substance by magnetic force from a first liquid container to a second liquid container through a passage disposed between the first and second liquid containers, the first liquid container storing a first liquid containing the magnetic particle to be a support of the detection target substance, the second liquid container storing a second liquid containing a labeled substance which is to form a complex together with the detection target substance and the magnetic particle; transporting the complex, which is formed in the second liquid container and contains the detection target substance, the magnetic particle, and the labeled substance, to a third liquid in a flow path; and transporting the magnetic particle to a detection tank where to detect the detection target substance, while agitating the magnetic particle in a mixed liquid of the complex and the third liquid within the flow path.

Another embodiment provides a sample analysis cartridge inserted into a sample analyzer that detects a detection target substance contained in a sample includes: a first liquid container that stores a first liquid containing a magnetic particle to be a support of the detection target substance; a second liquid container that stores a second liquid containing a labeled substance which is to form a complex together with the detection target substance and the magnetic particle; a passage that is disposed between the first liquid container and the second liquid container, and that transports the magnetic particle supporting the detection target substance to the second liquid container by magnetic force; and a first flow path that transports the complex formed in the second liquid container to a third liquid, the complex containing the detection target substance, the magnetic particle, and the labeled substance, wherein the magnetic particle is transported to a detection tank where to detect the detection target substance while being agitated in a mixed liquid of the complex and the third liquid in the first flow path.

Another embodiment provides a sample analyzer that analyzes a sample using a sample analysis cartridge including a first liquid container that stores a first liquid containing a magnetic particle to be a support of a detection target substance, a second liquid container that stores a second liquid containing a labeled substance which is to form a complex together with the detection target substance and the magnetic particle, a passage that is disposed between the first liquid container and the second liquid container, and that transports the magnetic particle supporting the detection target substance to the second liquid container by magnetic force, and a flow path that transports the complex, which is formed in the second liquid container, and contains the detection target substance, the magnetic particle, and the labeled substance, to a third liquid, wherein the magnetic particle is transported from inside of the flow path to a detection tank where to detect the detection target substance, while being agitated in a mixed liquid of the complex and the third liquid within the flow path.

EMBODIMENTS

With reference to the drawings, an embodiment is described below.

With reference to FIGS. 1 to 32, description is given of a sample analyzing method using cartridge 100 and a configuration of sample analysis cartridge 100 according to this embodiment.

(Overview of Sample Analysis Cartridge)

Figure 1:
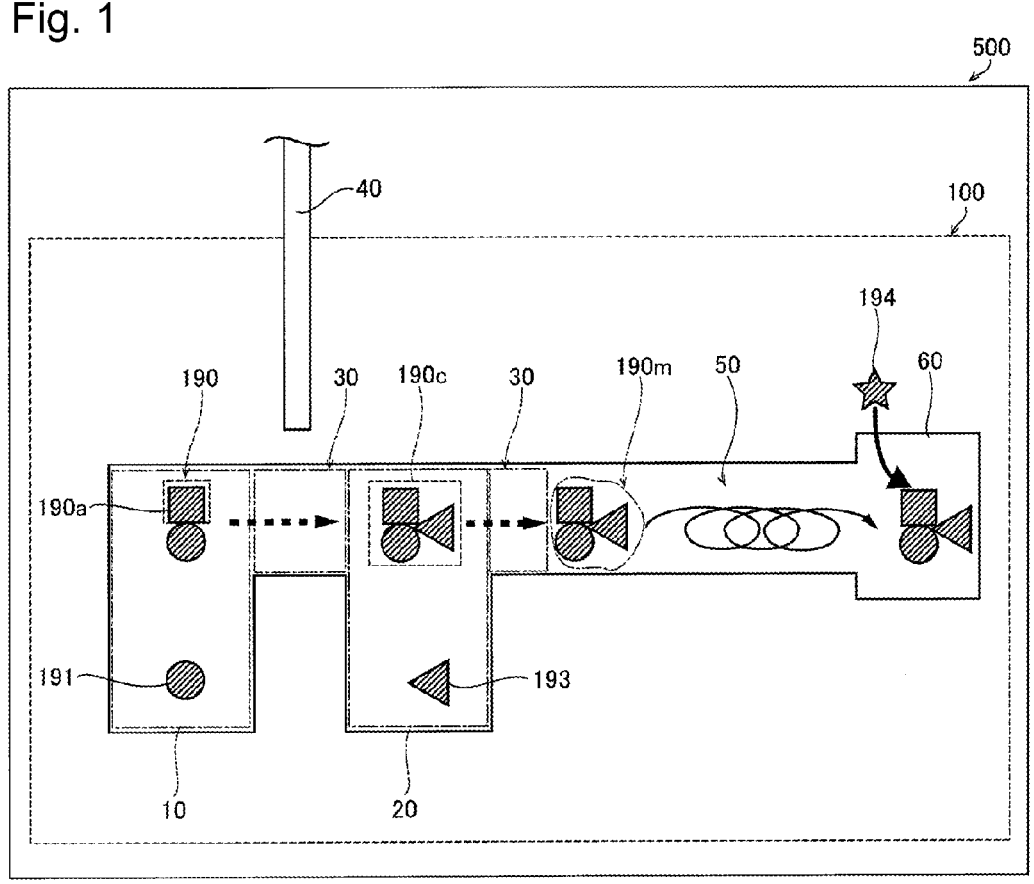
FIG. 1 is a diagram for explaining a sample analyzing method using a sample analysis cartridge.

FIG. 1 is a diagram for explaining a sample analyzing method using sample analysis cartridge (hereinafter referred to as cartridge) 100 to be inserted into sample analyzer 500 for detecting detection target substance 190a contained in sample 190. Sample 190 is, for example, blood.

Cartridge 100 includes first liquid container 10, second liquid container 20, and passage 30 disposed between first liquid container 10 and second liquid container 20. First liquid container 10 contains a first liquid. The first liquid contains magnetic particle 191 to be a support of detection target substance 190a. Second liquid container 20 contains a second liquid. The second liquid contains labeled substance 193 which is to form complex 190c together with detection target substance 190a and magnetic particle 191.

Passage 30 is connected to flow path 50. A portion of flow path 50 on the side opposite to the side connected to passage 30 is connected to detection tank 60 where to detect detection target substance 190a. Cartridge 100 is configured such that magnetic particle 191 is transported to detection tank 60 where to detect detection target substance 190a while being agitated in mixed liquid 190m of complex 190c and a third liquid in flow path 50. The third liquid is, for example, a buffer solution.

(Overview of Sample Analyzing Method)

A sample analyzing method using cartridge 100 is described.

First, magnetic particle 191 supporting detection target substance 190a is transported from first liquid container 10 to second liquid container 20 by magnetic force through passage 30 between first liquid container 10 and second liquid container 20. The magnetic force for transporting magnetic particle 191 within passage 30 is generated by magnetic source 40, for example.

Next, complex 190c, which is formed in second liquid container 20 and contains detection target substance 190a, magnetic particle 191, and labeled substance 193, is transported to the third liquid in flow path 50. As a force that transports formed complex 190c to flow path 50, the magnetic force can be used, which is generated by magnetic source 40 in sample analyzer 500, for example.

Then, magnetic particle 191 is transported to detection tank 60 while being agitated in mixed liquid 190m of complex 190c and the third liquid within flow path 50.

Various methods can be adopted as a method for agitating magnetic particle 191 in mixed liquid 190m of complex 190c and the third liquid within flow path 50. For example, magnetic particle 191 in mixed liquid 190m of complex 190c and the third liquid can be agitated within flow path 50 by moving mixed liquid 190m with an air pressure. The use of the air pressure can disperse magnetic particle 191 in mixed liquid 190m to be sufficiently agitated.

With the above configuration, magnetic particle 191 can be transported to detection tank 60 while being agitated in mixed liquid 190m of complex 190c and the third liquid within flow path 50. Thus, magnetic particle 191 agitated and dispersed in mixed liquid 190m can be transported to detection tank 60. As a result, luminescent reaction between labeled substance 193 contained in mixed liquid 190m and substrate 194 that is transported to detection tank 60 and facilitates light emission can be sufficiently caused in detection tank 60. Therefore, an adverse effect on detection accuracy of detection target substance 190a in detection tank 60 can be suppressed.

(Overview of Sample Analyzer)

Figure 2:
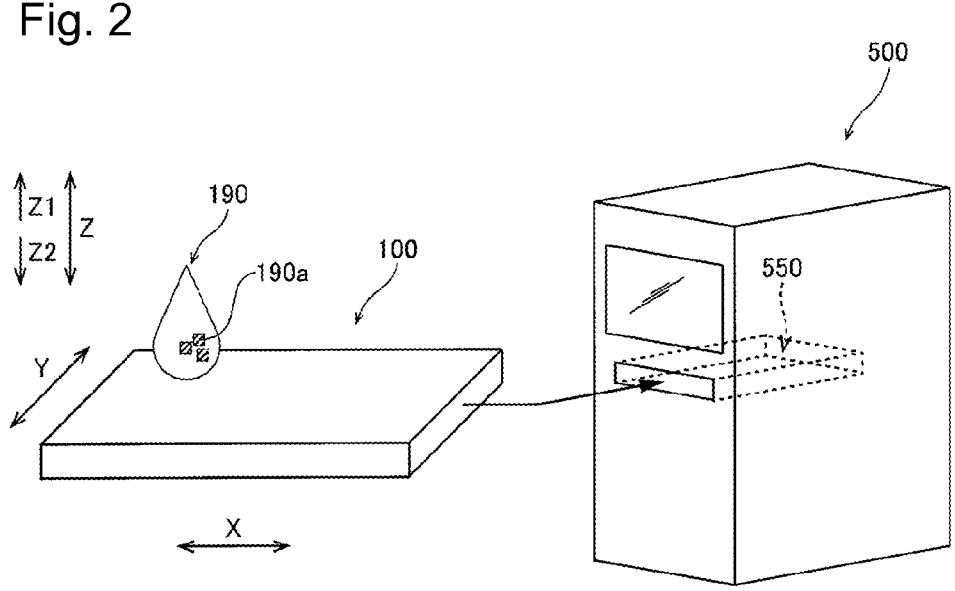
FIG. 2 is a diagram illustrating an overview of a sample analyzer.

FIG. 2 is a diagram illustrating an overview of sample analyzer 500. Sample analyzer 500 can determine whether or not there is detection target substance 190a in a specimen and can also determine the concentration of the detection target substance 190a in the specimen. Sample analyzer 500 has a size that can be installed on a desk in an examination room where a doctor examines a patient, for example. The installation area of sample analyzer 500 is as small as about 150 $cm^2$ to 300 $cm^2$, for example. Sample analyzer 500 is an apparatus for performing a test using disposable cartridge 100 to analyze a specimen. A liquid specimen, such as tissues, a body fluid, and a blood, obtained from the patient is injected into cartridge 100. Cartridge 100 having the specimen injected therein is inserted into set part 550 in sample analyzer 500. The specimen injected into cartridge 100 is analyzed by a predetermined assay based on functions of cartridge 100 and functions of sample analyzer 500.

(Configuration Example of Sample Analysis Cartridge)

Figure 3:
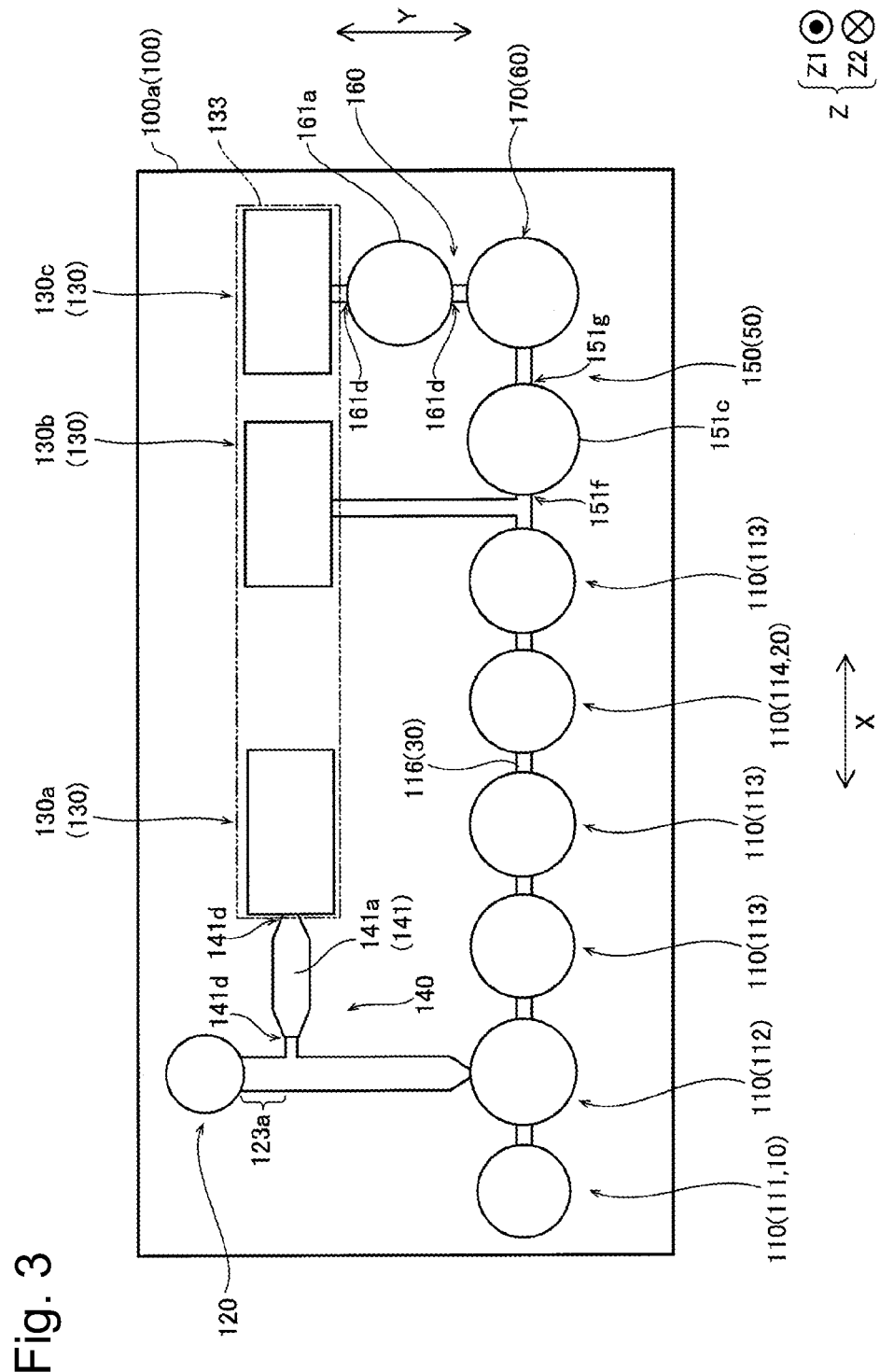
FIG. 3 is a plan view illustrating the sample analysis cartridge.

FIG. 3 is a diagram illustrating a configuration example of cartridge 100. Cartridge 100 is formed into a flat plate shape. Cartridge 100 includes liquid containers 110 containing liquids such as a specimen, a reagent and a cleaning solution. Liquid containers 110 contain R1 to R5 reagents. Some of the reagents contain magnetic particle 191 (see FIG. 5) that reacts with a substance containing detection target substance 190a (see FIG. 5). For example, the R2 reagent contains magnetic particle 191. Cartridge 100 includes sample-R1 reaction tank 112 that stores a liquid obtained by mixing a specimen and the R1 reagent. Cartridge 100 includes cleaning tank 113 that stores a cleaning solution for separating a reactant required for analysis of detection target substance 190a contained in sample 190 from other substances. Cartridge 100 includes detection tank 170 that stores a liquid containing a detection substance for detecting detection target substance 190a. Note that detection tank 170 is described as an example of detection tank 60 illustrated in FIG. 1. The R2 reagent is an example of the first liquid. The R3 reagent is an example of the second liquid. The R4 reagent is an example of the third liquid.

Note that, in the present specification, the "thickness direction of cartridge 100" is referred to as a Z direction. The front side in the Z direction is referred to as the Z1 size, while the back side in the Z direction is referred to as the Z2 side.

Note that, in the present specification, "to react" is a concept including "to couple" more than one substance.

In R2 reagent tank 111, sample-R1 reaction tank 112, cleaning tank 113, and R3 reagent tank 114, magnetic particle 191 is transported between the respective liquid containers, thereby progressing the reaction required for the analysis of sample 190. The specimen is put into blood cell separator 120 in cartridge 100. Blood cell separator 120 joins sample-R1 flow path 140 through sample inflow path 123a. Cartridge 100 includes air chambers 130. Air sent from air chambers 130 transports the liquids in some of liquid containers 110 in cartridge 100. Air chambers 130 are covered with sheet 133 made of an elastic member such as a rubber sheet. Air chambers 130 include first air chamber 130b. Air chambers 130 may also include air chamber 130a and second air chamber 130c.

(Configuration Example of Sample Analyzer)

Figure 4:
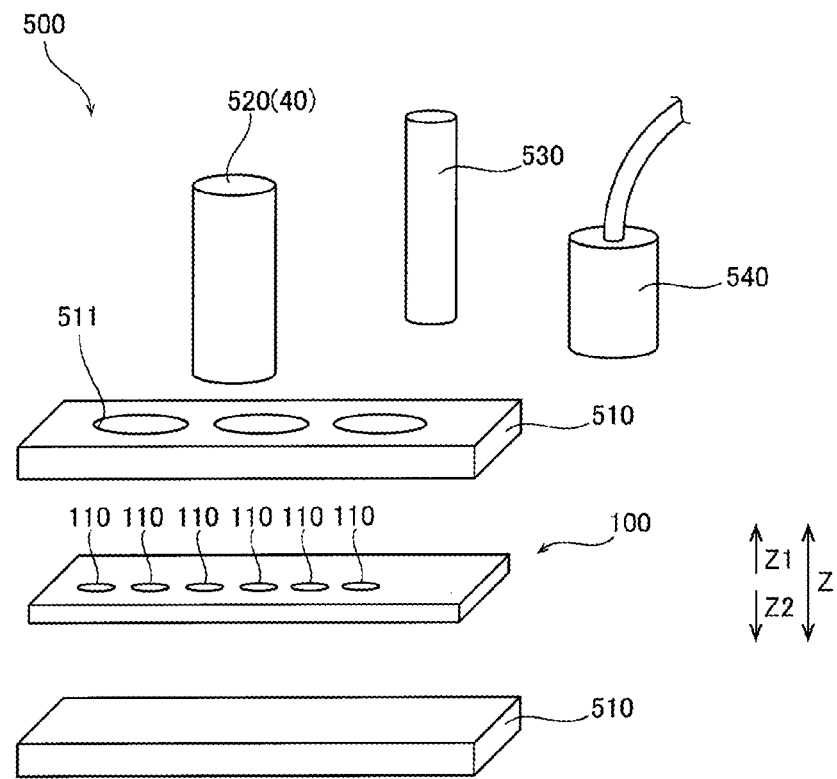
FIG. 4 is a diagram illustrating a configuration example of the sample analyzer.

FIG. 4 illustrates a configuration example of sample analyzer 500. Sample analyzer 500 includes heat blocks 510, magnet 520, plunger 530, and detector 540. Note that magnet 520 is described as an example of magnetic source 40 illustrated in FIG. 1.

Heat blocks 510 adjust the temperature of cartridge 100. Heat blocks 510 may be disposed so as to come into contact with the upper and lower surfaces of cartridge 100. Note that the upper surface of cartridge 100 is a surface corresponding to the direction in which magnet 520 for transporting magnetic particle 191 is disposed.

In sample analyzer 500, magnetic particle 191 (see FIG. 5) contained in some of liquid containers 110 in cartridge 100 is transported by magnetic force of magnet 520. Magnet 520 is a permanent magnet, for example. Magnet 520 is formed into an approximately cylindrical shape, for example.

In sample analyzer 500, plunger 530 can push down sheet 133 (see FIG. 3) covering air chambers 130 in cartridge 100. Air chambers 130 are contracted by pushing down sheet 133. Sample analyzer 500 can control the amount of air sent from air chambers 130 by adjusting how much the air chambers are pushed down by plunger 530. Sample analyzer 500 can adjust the amount of the liquids to be transported, by controlling the air amount. In sample analyzer 500, air chambers 130 can be returned to their initial state by sheet 133 returning plunger 530 that is pushed down. A negative pressure is generated when air chambers 130 are returned to the initial state. Sample analyzer 500 can transport the transported liquid in an opposite direction by the negative pressure. Some of the liquids in cartridge 100 are moved back and forth in a flow path inside cartridge 100 by the vertical movement of plunger 530.

Heat block 510 includes holes 511 for magnet 520 and plunger 530 to access cartridge 100. Holes 511 are provided in heat block 510 disposed on the upper surface of cartridge 100, for example. When magnet 520 and plunger 530 access cartridge 100 from both directions, holes 511 may be provided in both of heat blocks 510 disposed on the both sides of cartridge 100 in the Z direction. Some of holes 511 may be recesses that do not penetrate heat block 510.

Detector 540 detects light generated by a reactant generated by reaction between sample 190 and a reagent. Detector 540 is, for example, a photomultiplier tube.

(Explanation of Assay)

Figure 5:
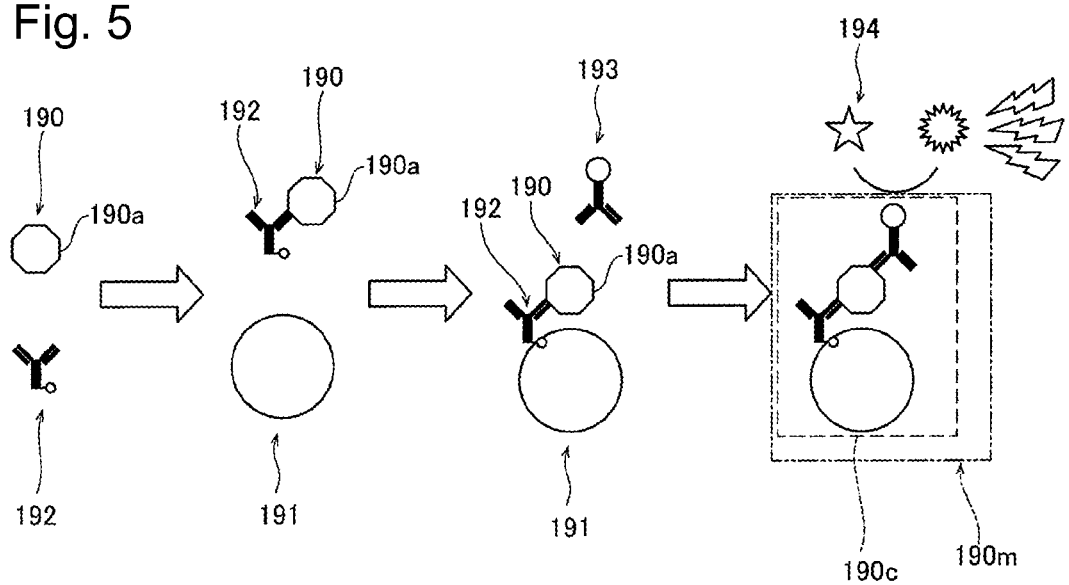
FIG. 5 is a diagram illustrating an overview of assay.
Figure 6:
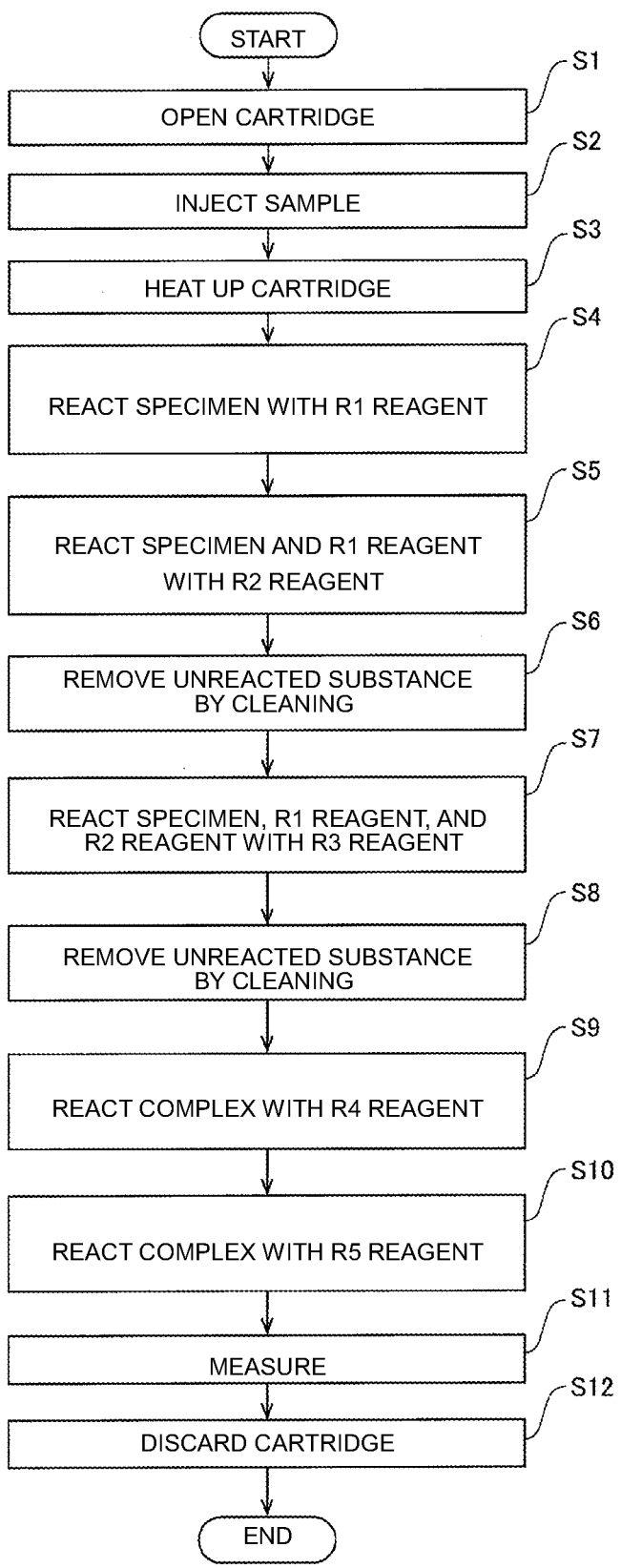
FIG. 6 is a flowchart illustrating an operation example when the assay is implemented.

With reference to FIG. 5, an overview of assay is described.

Detection target substance 190a in sample 190 includes, for example, an antigen or an antibody. The antigen is a hepatitis B surface antigen (HBsAg), for example.

The R1 reagent contains capture substance 192 to be coupled to detection target substance 190a. The R1 reagent can be selected according to detection target substance 190a. Capture substance 192 includes an antibody or an antigen. The antibody is a biotin-coupled HBs monoclonal antibody, for example.

Detection target substance 190a coupled to capture substance 192 is coupled to magnetic particle 191 in the R2 reagent. Magnetic particle 191 serves as a support of detection target substance 190a. Magnetic particle 191 is, for example, a streptavidin-coupled magnetic particle having its surface coated with avidin. The avidin of magnetic particle 191 is likely to be coupled to the biotin of the R1 reagent. Thus, connectivity between magnetic particle 191 and capture substance 192 is improved.

The coupled body of detection target substance 190a, capture substance 192, and magnetic particle 191 is separated from an unreacted substance by cleaning with a cleaning solution.

After the cleaning, the coupled body of detection target substance 190a, capture substance 192, and magnetic particle 191 reacts with labeled substance 193 in the R3 reagent. Labeled substance 193 includes, for example, a labeled antibody. The labeled antibody is an ALP labeled HBsAg monoclonal antibody.

Labeled substance 193 is coupled to detection target substance 190a, for example. Labeled substance 193 may be coupled to capture substance 192 or may be coupled to magnetic particle 191.

A reactant obtained by reacting at least detection target substance 190a and magnetic particle 191 with labeled substance 193 is called "complex 190c". Complex 190c may contain capture substance 192, for example.

Complex 190c is separated from the unreacted substance by cleaning with the cleaning solution.

After the cleaning, complex 190c is combined with the R4 reagent. A reactant obtained by reacting complex 190c with the R4 reagent is called "mixed liquid 190m". The R4 reagent has a composition that facilitates light emission by complex 190c. The R4 reagent is, for example, a buffer solution.

The R5 reagent is added to mixed liquid 190m. The R5 reagent includes, for example, substrate 194 that reacts with complex 190c to facilitate light emission.

Complex 190c reacts with the R5 reagent to emit light. Detector 540 measures emission intensity of the light emitted by complex 190c.

Note that detection target substance 190a, capture substance 192, magnetic particle 191, and labeled substance 193 may be a combination other than the above. For example, detection target substance 190a, capture substance 192, magnetic particle 191, and labeled substance 193 may be a TP antibody, a biotin-coupled TP antigen, a streptavidin-coupled magnetic particle, and an ALP labeled TP antigen, respectively. Alternatively, detection target substance 190a, capture substance 192, magnetic particle 191, and labeled substance 193 may be an HCV antibody, a biotin-coupled HCV antigen, an HCV antigen immobilized magnetic particle, and an ALP labeled anti-human IgG monoclonal antibody, respectively. Alternatively, detection target substance 190a, capture substance 192, magnetic particle 191, and labeled substance 193 may be an FT4, a biotin-coupled anti-T4 monoclonal antibody, a streptavidin-coupled magnetic particle, and an ALP labeled T3, respectively.

Alternatively, detection target substance 190a may be any of an HIV-1p24 antigen and an anti-HIV antibody. Capture substance 192 may be a biotin-coupled anti-HIV-1p24 antibody. Magnetic particle 191 may be a coupled magnetic particle having streptavidin and immobilized HIV antigen. Labeled substance 193 may be any of an ALP labeled HIV-1p24 antibody and an ALP labeled HIV antigen.

(Explanation of Assay)

With reference to FIGS. 3 to 7, description is given of an operation example when the above assay is executed using sample analyzer 500 and cartridge 100.

In Step S1, cartridge 100 is opened from a package by a user.

In Step S2, a specimen obtained from a patient is put into blood cell separator 120 in the opened cartridge 100. After the specimen is put into cartridge 100, cartridge 100 is inserted into sample analyzer 500. The specimen put into cartridge 100 stops after flowing from blood cell separator 120 up to a location in sample-R1 flow path 140 near sample-R1 reaction tank 112.

In Step S3, heat blocks 510 (see FIG. 4) adjust the temperature of the inserted cartridge 100. For example, heat blocks 510 heat up cartridge 100.

In Step S4, sample analyzer 500 reacts the antigen contained in detection target substance 190a with the antibody contained in the R1 reagent. Sample analyzer 500 uses plunger 530 (see FIG. 4) to push down air chamber 130a. The R1 reagent is pushed out to sample-R1 flow path 140, through which the specimen flows, by the air sent from air chamber 130a. Sample analyzer 500 moves up and down plunger 530. The specimen and the R1 reagent are moved back and forth within the flow path by a negative pressure and a positive pressure, which are alternately generated according to the up-and-down movement of plunger 530. The back-and-forth movement within the flow path facilitates the reaction between detection target substance 190a and capture substance 192. Sample analyzer 500 further pushes down plunger 530 to push out the specimen and the R1 reagent to sample-R1 reaction tank 112.

In S5, sample analyzer 500 reacts detection target substance 190a and capture substance 192 with magnetic particle 191 contained in the R2 reagent. Sample analyzer 500 uses magnet 520 to draw magnetic particle 191 close to the liquid surface in R2 reagent tank 111. Sample analyzer 500 uses the magnetic force of magnet 520 to transport the drawn magnetic particle 191 from R2 reagent tank 111 to sample-R1 reaction tank 112. Sample analyzer 500 uses the magnetic force of magnet 520 to agitate magnetic particle 191, thereby reacting magnetic particle 191 with detection target substance 190a and capture substance 192. Note that R2 reagent tank 111 is described as an example of first liquid container 10 illustrated in FIG. 1.

In S6, sample analyzer 500 uses the magnetic force of magnet 520 to transport magnetic particle 191 reacted with detection target substance 190a and capture substance 192 to cleaning tank 113. Sample analyzer 500 agitates detection target substance 190a and capture substance 192 as well as magnetic particle 191 in cleaning tank 113. Magnetic particle 191 reacted with detection target substance 190a and capture substance 192 is separated from an unreacted substance.

In S7, sample analyzer 500 uses the magnetic force of magnet 520 to transport magnetic particle 191 reacted with detection target substance 190a and capture substance 192 to R3 reagent tank 114. Sample analyzer 500 agitates magnetic particle 191 reacted with detection target substance 190a and capture substance 192. Thus, magnetic particle 191 reacted with detection target substance 190a and capture substance 192 reacts with labeled substance 193 contained in the R3 reagent, thereby generating complex 190c containing capture substance 192. Note that R3 reagent tank 114 is described as an example of second liquid container 20 illustrated in FIG. 1.

In S8, sample analyzer 500 uses the magnetic force of magnet 520 to transport complex 190c containing capture substance 192 to the cleaning tank. Sample analyzer 500 agitates complex 190c containing capture substance 192 in cleaning tank 113. Thus, complex 190c containing capture substance 192 is separated from an unreacted substance.

In S9, sample analyzer 500 uses the magnetic force of magnet 520 to transport complex 190c containing capture substance 192 to R4 reagent tank 151c. Complex 190c containing capture substance 192 is combined with a buffer solution in R4 reagent tank 151c. Sample analyzer 500 uses plunger 530 to push down first air chamber 130b. Thus, mixed liquid 190m of complex 190c containing capture substance 192 and the R4 reagent is pushed out to first flow path 150. Sample analyzer 500 moves up and down plunger 530, thereby moving mixed liquid 190m back and forth in first flow path 150. Sample analyzer 500 further pushes down plunger 530 to push out mixed liquid 190m to detection tank 170. Note that first flow path 150 is described as an example of flow path 50 illustrated in FIG. 1.

In Step S10, substrate 194 contained in the R5 reagent is added to mixed liquid 190m. Sample analyzer 500 uses plunger 530 to push down second air chamber 130c, thereby pushing out the R5 reagent to detection tank 170. The R5 reagent pushed out to detection tank 170 is added to mixed liquid 190m in detection tank 170.

In Step S11, detector 540 detects light generated by the reaction between substrate 194 and labeled substance 193 contained in mixed liquid 190m. Detector 540 measures emission intensity of the light, for example.

In Step S12, cartridge 100 is taken out of sample analyzer 500 by the user and discarded upon completion of the measurement. Cartridge 100 to be discarded generates no waste liquid.

[Configuration of Respective Parts in Sample Analysis Cartridge]

(Configuration of Liquid Container)

At least some of liquid containers 110 illustrated in FIG. 3 have a structure to suppress mixing of the liquid disposed in the surface of liquid container 110 and the liquid disposed in the surface of another liquid container 110.

In this embodiment, R2 reagent tank 111, sample-R1 reaction tank 112, cleaning tank 113, R3 reagent tank 114, and R4 reagent tank 151c have the structure to suppress mixing of the liquid in liquid container 110 and the liquid in another liquid container 110. R2 reagent tank 111, sample-R1 reaction tank 112, cleaning tank 113, R3 reagent tank 114, and R4 reagent tank 151c are connected in series through a gas-phase space in passage 116. Passage 116 includes passage 30 illustrated in FIG. 1.

Note that the gas-phase space means a space filled with gas, through which magnetic particle 191 invariably passes when magnetic particle 191 is transported from the liquid in one of liquid containers 110 to the liquid in liquid container 110 adjacent thereto. Note that the inside of passage 116 may be entirely set as the gas-phase space or may be partially set as the gas-phase space. To be more specific, a part of a transportation path of magnetic particle 191 in passage 116 between two adjacent liquid containers 110 may be set as the gas-phase space. Note that, as for the gas, air is preferably used, but nitrogen or the like can also be used.

Sample analyzer 500 executes the assay by transporting magnetic particle 191 through the gas-phase space in passage 116 between liquid containers 110. Thus, sample analyzer 500 can execute the assay for analysis while suppressing the liquid in liquid container 110 from being mixed into the liquid in liquid container 110 adjacent thereto by the movement of magnetic particle 191. When the liquid contained in liquid container 110 is mixed into the liquid contained in another liquid container 110 by the movement of magnetic particle 191, reaction conditions change in the liquid in another liquid container 110. Such a change in reaction conditions reduces a reaction effect of the sample and the substance in the reagent. As a result, there may be influence on accuracy and the like of the measurement result obtained by sample analyzer 500. Therefore, the analysis accuracy of sample analyzer 500 is improved by suppressing mixing of the liquid contained in liquid container 110 into the liquid contained in another liquid container 110. Moreover, it is no longer required to consider the compatibility between the liquids contained in liquid containers 110 by suppressing the mixing of the liquid contained in liquid container 110 into the liquid contained in another liquid container 110. Thus, the degree of freedom of selection of the liquids contained in liquid containers 110 is increased. As a result, combinations of reagents corresponding to various test items can be contained in liquid containers 110. Since various combinations of reagents can be contained in liquid containers 110, the type of the cartridge can be diversified.

Figure 7:
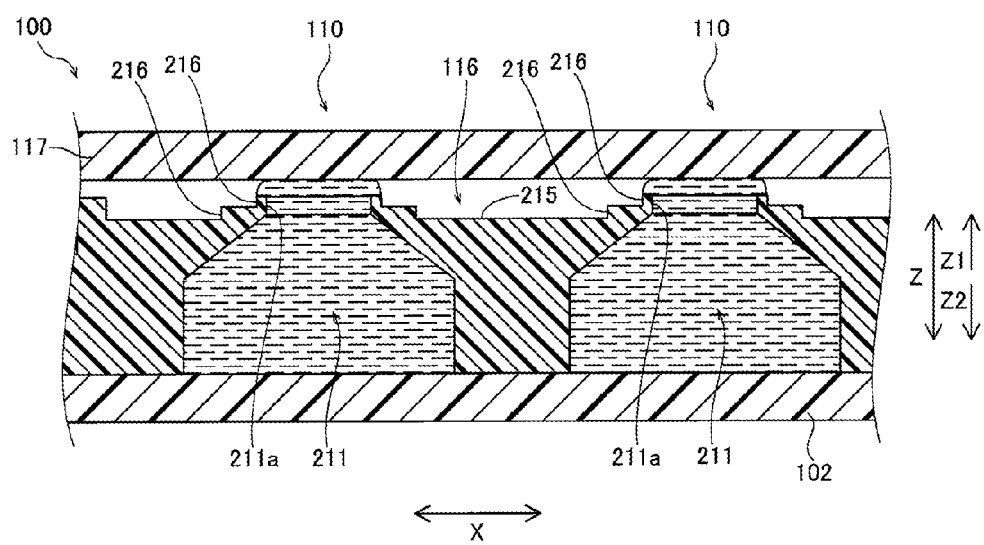
FIG. 7 is a diagram illustrating a structure to suppress mixing of liquids.

Meanwhile, at least some of liquid containers 110 have a liquid storage portion communicated with a surface region connected to passage 116 through an opening. More specifically, liquid container 110 may have liquid storage part 211 having passage-side opening 211a and having a recessed shape capable of storing a liquid inside. In this embodiment, R2 reagent tank 111, cleaning tank 113, R3 reagent tank 114, and R4 reagent tank 151c each have liquid storage part 211. As illustrated in FIG. 7, step 216 is provided around opening 211a. The liquid contained in liquid container 110 may be not only in liquid storage part 211 but also in passage 116 above liquid container 110.

Magnetic particle 191 transported from liquid container 110 through passage 116 can be moved into liquid storage part 211 from passage-side opening 211a. Liquid storage part 211 can easily increase the amount of liquid. Thus, compared with the case where magnetic particle 191 is dispersed into the liquid disposed only in the surface of liquid container 110, magnetic particle 191 can be dispersed efficiently into the liquid.

Figure 8:
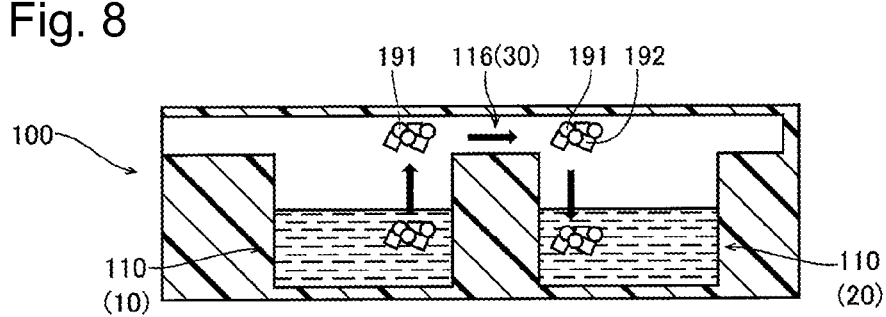
FIG. 8 is a diagram illustrating a layout example of liquid containers and a passage.

FIG. 8 illustrates a layout example of liquid containers 110 and passage 116 connecting adjacent liquid containers 110. In the example illustrated in FIG. 8, passage 116 is disposed above liquid containers 110. Magnetic particle 191 is pulled up to the gas-phase space in passage 116 by the magnetic force from liquid container 110, and transported to another liquid container 110.

Figure 9:
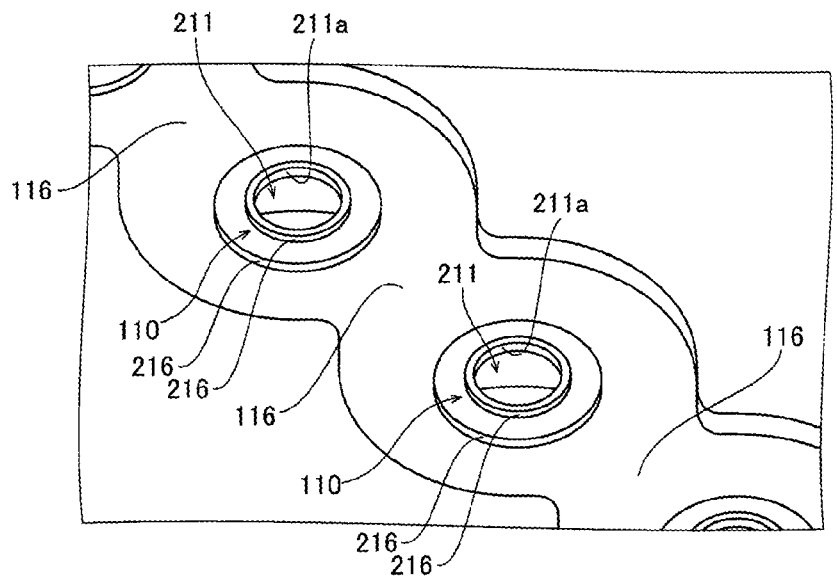
FIG. 9 is a diagram illustrating the liquid containers as seen from above.

As illustrated in FIG. 9, passage 116 is provided near the outer surface of cartridge 100, and is formed along the outer surface of cartridge 100. In this case, magnet 520 in sample analyzer 500 disposed outside cartridge 100 can come close to passage 116. Thus, stronger magnetic force can be generated to act on magnetic particle 191 for efficient transportation of magnetic particle 191. Moreover, the magnetic force to be generated by magnet 520 can be reduced for how close magnet 520 can come to passage 116. Thus, magnet 520 can be reduced in size, and sample analyzer 500 can also be reduced in size.

Step 216 around opening 211a is disposed so as to separate one liquid container 110 from another liquid container 110. Step 216 is disposed so as to separate liquid containers 110 from passage 116.

In this embodiment, the liquids in different liquid containers 110 can be inhibited from being mixed with each other through the gas-phase space in passage 116. As a result, contamination between liquid containers 110 can be suppressed.

Step 216 is provided at the end of liquid container 110. Also, step 216 is provided along the periphery of opening 211a, for example. When opening 211a is circular, step 216 may be formed into an annular shape surrounding the peripheral part of opening 211a.

Cartridge 100 includes cover part 117 on the Z1 side, which covers liquid containers 110 and passage 116. Cover part 117 sandwiches the liquids between liquid containers and cover part 117. Cover part 117 comes into contact with the upper surface of the liquid in passage 116 above liquid container 110. Moreover, cartridge 100 has the Z2-side surface covered with sheet 102.

In the configuration example of FIG. 7, cover part 117 covers passage 116 from the upper surface side.

Cover part 117 includes a flat sheet member, for example. Cover part 117 may be formed using a material having a hydrophobic surface on the liquid container 110 side. The hydrophobic material may be a coating material provided on the surface of the sheet member of cover part 117. The sheet member itself included in cover part 117 may be formed using a hydrophobic material. Cartridge main body 100a may be formed such that cartridge main body 100a has a hydrophobic surface on the Z1 side.

FIG. 9 is a diagram illustrating the liquid containers as seen from above. Step 216 is provided at passage-side opening 211a in liquid container 110. Step 216 is provided along the outer shape of passage-side opening 211a, for example. Step 216 is formed between passage-side opening 211a and a peripheral part of passage-side opening 211a.

FIG. 9 illustrates the example where two steps 216 are provided. However, the number of steps 216 can be changed as appropriate.

(Sample-R1 Reaction Tank)

Figure 10A:
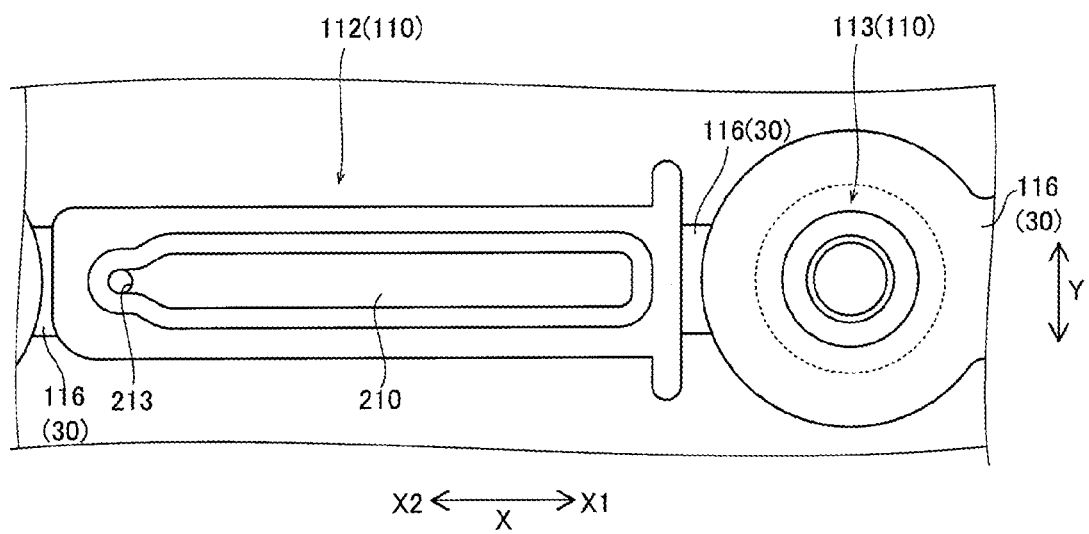
FIG. 10A and FIG. 10B are diagrams illustrating a sample-R1 reaction tank.
Figure 10B:
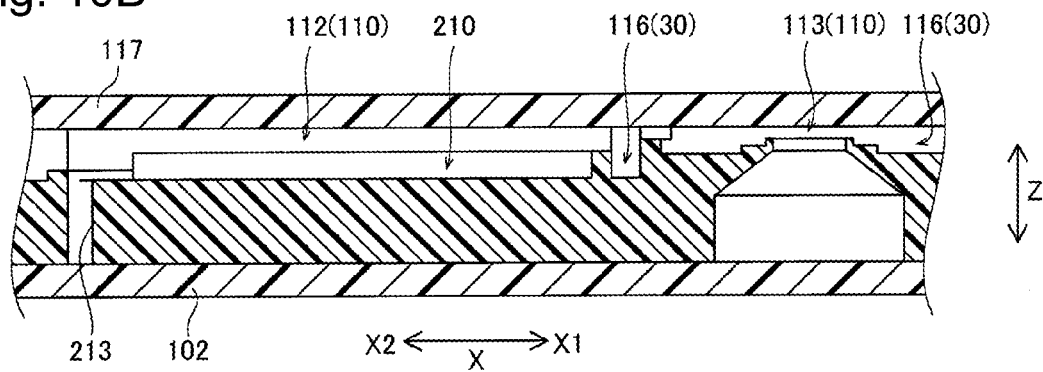

FIG. 10A and FIG. 10B illustrate a configuration example of sample-R1 reaction tank 112. In cartridge 100, the specimen flowing in from blood cell separator 120 is mixed with the R1 reagent on a flow path, and then discharged to sample-R1 reaction tank 112.

Sample-R1 reaction tank 112 includes inlet 213 for supplying the mixed liquid of the specimen and the R1 reagent to the inside of the tank. Inlet 213 is disposed in a peripheral portion of liquid disposition position 210. FIG. 10A and FIG. 10B illustrate a configuration example where liquid disposition position 210 extends linearly in the X direction. In this case, inlet 213 is disposed at the end of liquid disposition position 210. Inlet 213 is an opening formed in the surface (bottom) of liquid disposition position 210, for example. Note that, in the present specification, the "longitudinal direction of cartridge 100" is referred to as the X direction. Moreover, the "short direction of cartridge 100" is referred to as the Y direction.

In the configuration example of FIG. 10A and FIG. 10B, the mixed liquid of the specimen and the R1 reagent flowing in through inlet 213 spreads in the X1 direction from inlet 213 that is one end of liquid disposition position 210 to the other end.

At liquid disposition position 210, the mixed liquid of the specimen and the R1 reagent spreads across liquid disposition position 210. Thus, the area of the mixed liquid of the specimen and the R1 reagent transported to sample-R1 reaction tank 112 is increased to facilitate mixing of detection target substance 190a in the mixed specimen and capture substance 192 in the R1 reagent with magnetic particle 191.

Figure 11:
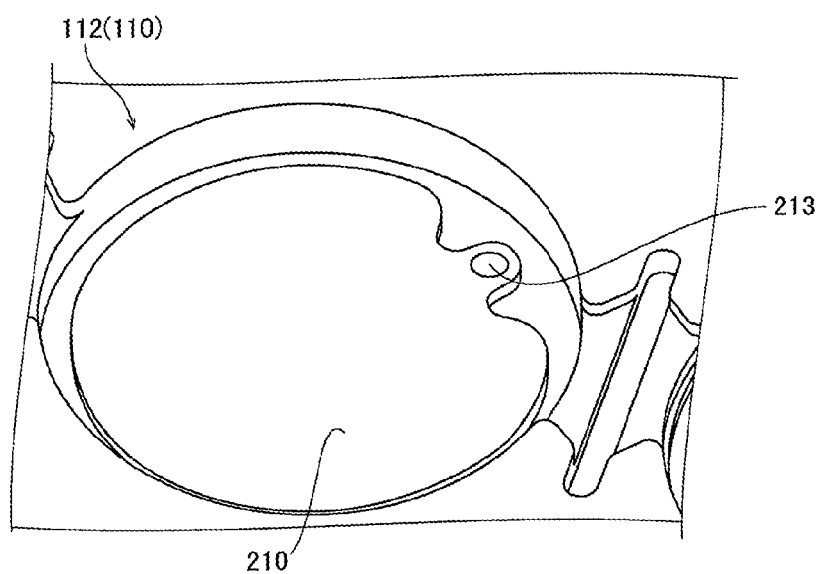
FIG. 11 is a diagram illustrating another configuration example of the sample-R1 reaction tank.

FIG. 11 illustrates another configuration example of sample-R1 reaction tank 112.

Sample-R1 reaction tank 112 may have a shape other than the linearly extending shape. Here, sample-R1 reaction tank 112 has approximately circular liquid disposition position 210. Inlet 213 is disposed in the surface of a peripheral portion of liquid disposition position 210.

(Cleaning Tank)

Figure 12A:
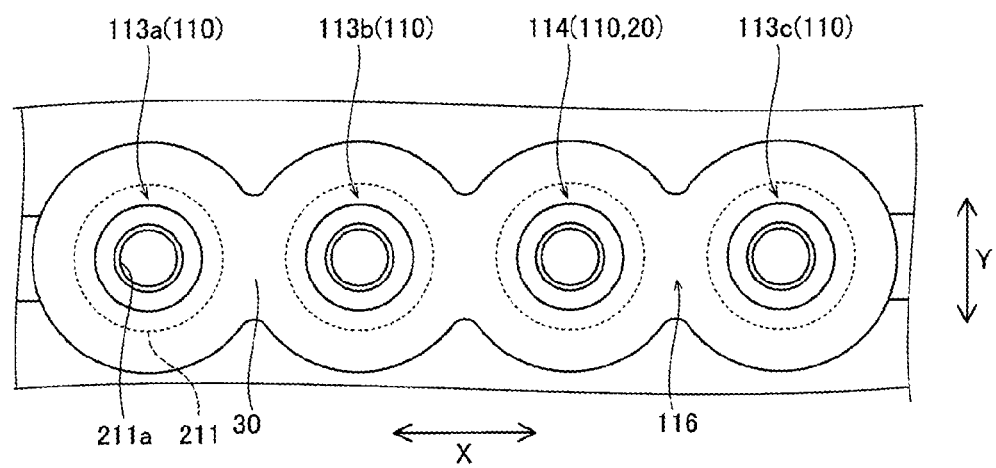
FIG. 12A and FIG. 12B are diagrams illustrating a cleaning tank and a reagent tank.
Figure 12B:
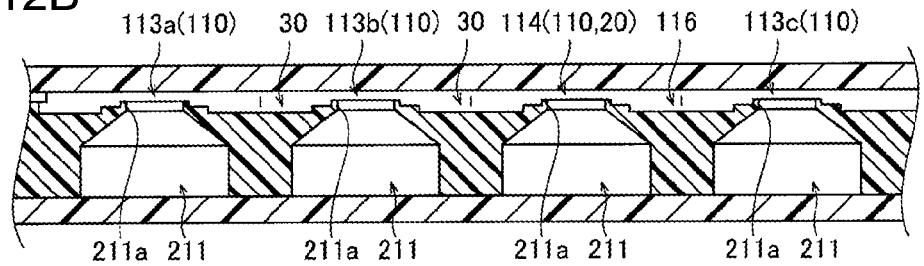

As illustrated in FIG. 12A and FIG. 12B, cleaning tank 113 is disposed between reagent tanks for reacting magnetic particle 191 with the reagents, which are transported by the magnetic force. With such arrangement of cleaning tank 113, magnetic particle 191 is transported to a next reagent tank after cleaned in cleaning tank 113. Thus, carryover of unreacted substances to the next reagent tank can be suppressed. Cleaning tanks 113 may be arranged between the reagent tanks. For example, cleaning tank 113a and cleaning tank 113b are between sample-R1 reaction tank 112 and R3 reagent tank 114, and cleaning tank 113c is between R3 reagent tank 114 and R4 reagent tank 151c.

Cleaning tanks 113a to 113c may be configured to include liquid storage part 211 having passage-side opening 211a. In this case, the cleaning solution in liquid storage part 211 can be connected to the cleaning solution disposed above passage-side opening 211a through passage-side opening 211a. Thus, magnetic particle 191 transported by the magnetic force can be dispersed into the cleaning solution in liquid storage part 211 through passage-side opening 211a. As a result, the amount of the cleaning solution into which magnetic particle 191 is dispersed can be increased. Thus, cleaning efficiency can be improved.

Note that, in this embodiment, magnetic particle 191 is transported through the gas-phase space. Thus, there is very little carryover of the liquid adhering to magnetic particle 191 transported to passage 116.

(R3 Reagent Tank)

As for R3 reagent tank 114, for example, the same configuration as that of cleaning tanks 113a to 113c can be adopted. When liquid storage part 211 is provided in R3 reagent tank 114, the amount of the R3 reagent, into which magnetic particle 191 is dispersed, can be increased. Thus, reaction efficiency can be improved.

(Transportation of Magnetic Particles)

In this embodiment, sample analyzer 500 transports magnetic particles 191 between the liquids disposed on the surfaces of liquid containers 110. During the process of transporting magnetic particles 191 between the liquids, the antibody, antigen and the like contained in the liquids adhere to magnetic particles 191, and reaction required for the assay progresses. Thus, the liquid contained in liquid container 110 is inhibited from being mixed into the liquid contained in another liquid container 110 by the movement of magnetic particles 191.

Figure 13:
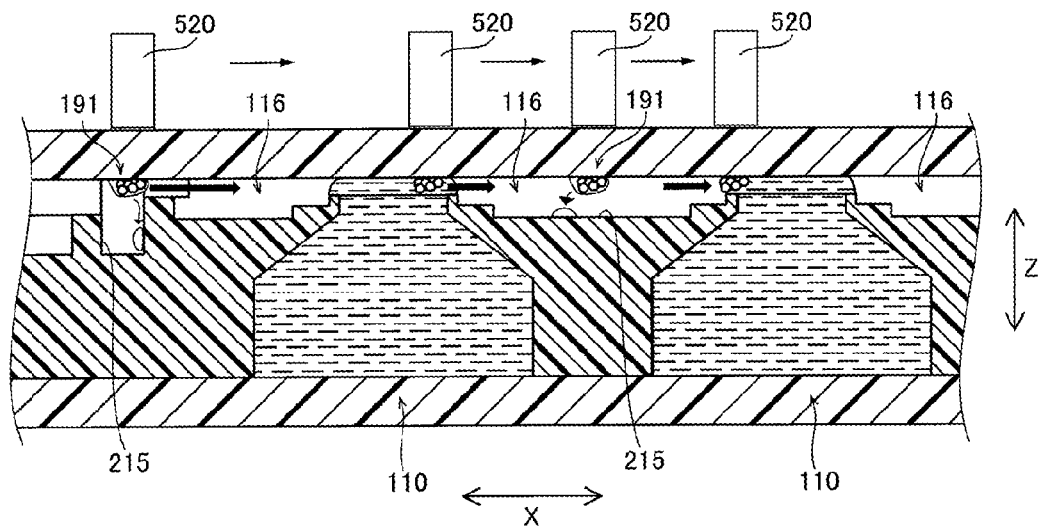
FIG. 13 is a diagram illustrating a structure to remove a liquid adhering to magnetic particles.
Figure 14:
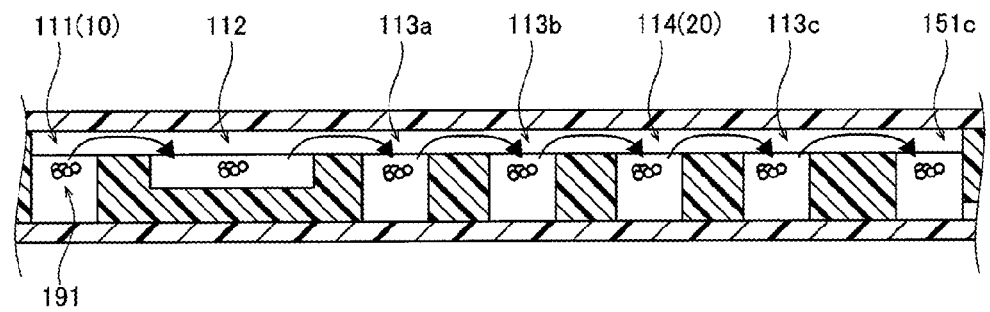
FIG. 14 is a diagram illustrating a state where the magnetic particles are transported by magnetic force.

FIG. 13 illustrates an overview of the transportation of magnetic particles 191 between liquid containers 110.

Sample analyzer 500 moves magnet 520 close to liquid container 110 in cartridge 100, thereby aggregating magnetic particles 191 near opening 211a of liquid container 110. Sample analyzer 500 moves magnet 520 to transport magnetic particles 191. Sample analyzer 500 moves magnet 520 to transport the aggregated magnetic particles 191 to the gas-phase space in passage 116 from a gas-liquid interface. The magnetic force of magnet 520 transports the aggregated magnetic particles 191 to the gas-phase space in passage 116 from the gas-liquid interface. Sample analyzer 500 further moves magnet 520 to transport aggregated magnetic particles 191 to the liquid in another liquid container 110.

Liquid containers 110 associated with the transportation of magnetic particles 191 may be arranged linearly in the longitudinal direction of cartridge 100. By linearly arranging liquid containers 110, magnetic particles 191 can be inhibited from remaining in liquid containers 110 and passage 116.

The liquid may adhere to magnetic particles 191 transported to passage 116 from the gas-liquid interface. As illustrated in FIG. 13, liquid containers 110 in sample analysis cartridge 100 may have a structure to further suppress the liquid contained in liquid container 110 from being mixed into the liquid contained in another liquid container 110 by the movement of magnetic particles 191. For example, grooves 215 may be provided by deeply denting the surface of passage 116. Thus, a structure may be realized, in which the liquid adhering to magnetic particles 191 is likely to fall onto the bottoms of grooves 215 from passage 116. Moreover, the liquid may leak into grooves 215 from liquid containers 110.

The liquids in respective liquid containers 110 may leak into passage 116 through openings 211a as long as the amount of the liquid leaking into passage 116 is not as large as that is mixed with the liquid in another liquid container 110 and the gas-phase space remains in passage 116. In this case, even if the liquid leaks out to passage 116, magnetic particles 191 are transported to adjacent liquid container 110 through the gas-phase space in passage 116. Thus, the liquid contained in liquid container 110 can be inhibited from being mixed into the liquid contained in another liquid container 110 by the movement of magnetic particles 191. When a structure is provided to further suppress the liquid contained in liquid container 110 from being mixed into the liquid contained in another liquid container 110 by the movement of magnetic particles 191, the liquid contained in liquid container 110 can be further inhibited from being mixed into the liquid contained in another liquid container 110 by the movement of magnetic particles 191. For example, when recessed grooves are provided in passage 116, even if the liquid contained in liquid container 110 is mixed with the liquid contained in another liquid container 110 in the groove, magnetic particles 191 are transported to adjacent liquid container 110 through the gas-phase space in passage 116. Thus, the liquid contained in liquid container 110 can be further inhibited from being mixed into the liquid contained in another liquid container 110 by the movement of magnetic particles 191.

(Transportation of Magnetic Particles to Respective Liquid Containers)

Here, description is given of transportation of magnetic particles 191 between two liquid containers. In a configuration example illustrated in FIG. 14, magnetic particles 191 are transported by the magnetic force to sample-R1 reaction tank 112, cleaning tank 113a, cleaning tank 113b, R3 reagent tank 114, cleaning tank 113c, and R4 reagent tank 151c in this order, starting from R2 reagent tank 111 on the upstream side in the transportation direction.

Magnetic particles 191 transported from R2 reagent tank 111 by the magnetic force are mixed with detection target substance 190a and capture substance 192 in the R1 reagent in sample-R1 reaction tank 112. Sample-R1 reaction tank 112 contains a reaction liquid containing detection target substance 190a, magnetic particles 191, and capture substance 192.

The liquid disposed in sample-R1 reaction tank 112 is the reaction liquid containing detection target substance 190a, magnetic particles 191, and capture substance 192. The liquid disposed in cleaning tank 113a is a cleaning solution. Magnetic particles 191 supporting detection target substance 190a are transported into the cleaning solution in cleaning tank 113a by magnet 520.

A cleaning solution is disposed in cleaning tank 113b. Only magnetic particles 191 supporting detection target substance 190a are transported by the magnetic force between cleaning tank 113a and cleaning tank 113b. Therefore, the cleaning solution in cleaning tank 113a can be inhibited from being brought into cleaning tank 113b. Thus, unwanted substances dispersed into the cleaning solution in cleaning tank 113a can be inhibited from being transported to cleaning tank 113b. Thus, cleaning processing can be effectively performed. As a result, the number of times of the cleaning processing (that is, the number of the cleaning tanks) can be reduced. The unwanted substances include components other than detection target substance 190a contained in the specimen, components unreacted with detection target substance 190a contained in the reagent, and the like.

R3 reagent tank 114 contains a labeled reagent containing labeled substance 193. Magnetic particles 191 supporting detection target substance 190a are transported from cleaning tank 113b to R3 reagent tank 114. Then, detection target substance 190a reacts with labeled substance 193.

Cleaning tank 113c contains a cleaning solution. In cleaning tank 113c, magnetic particles 191 supporting detection target substance 190a are cleaned. Between R3 reagent tank 114 and cleaning tank 113c, again, the liquid can be inhibited from being brought from R3 reagent tank 114 into cleaning tank 113c. Thus, the cleaning processing can be effectively performed by reducing brought unwanted substances. As a result, the unwanted substances can be inhibited from being transported to detection tank 170. Thus, reduction in detection accuracy can be effectively suppressed.

R4 reagent tank 151c contains a buffer solution. Magnetic particles 191 transported from cleaning tank 113c to R4 reagent tank 151c is dispersed into the buffer solution in R4 reagent tank 151c.

(Agitation Operation)

Figure 15A:
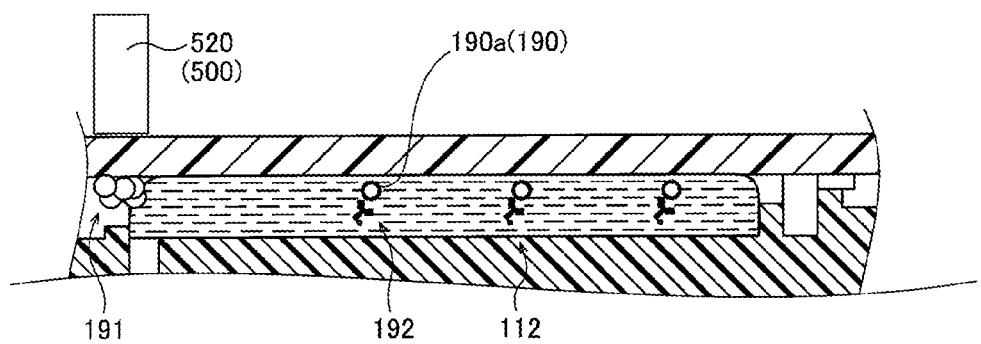
FIG. 15A to FIG. 15C are diagrams illustrating an example of an agitation operation using the magnetic force.
Figure 15B:
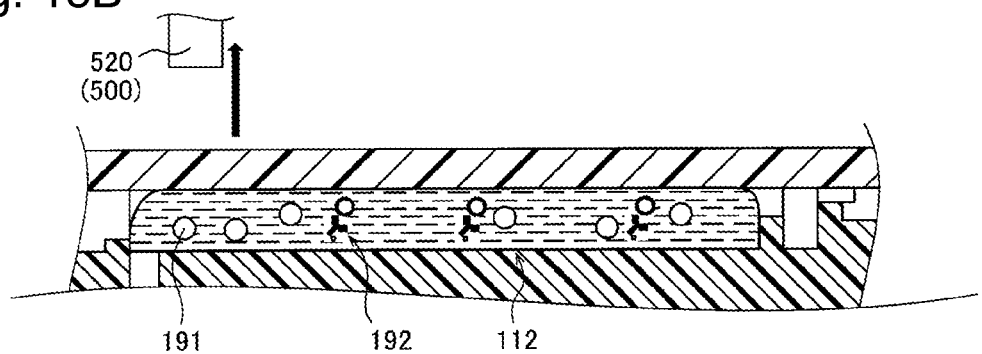
Figure 15C:
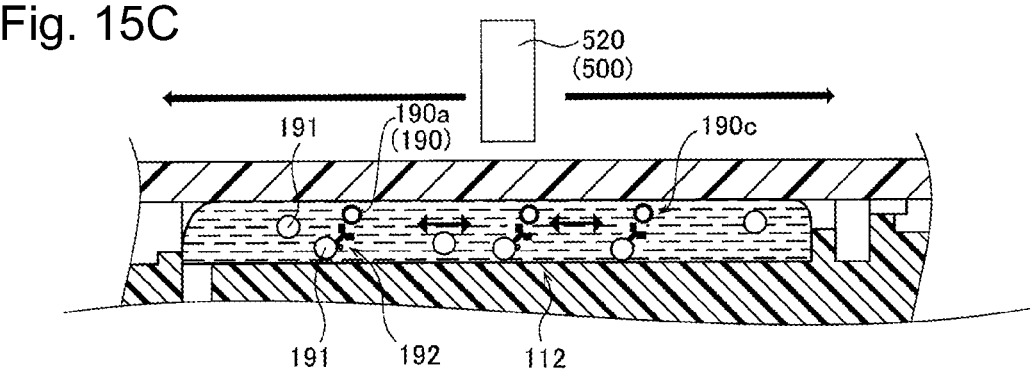

FIGS. 15A to 15C illustrate an example of an agitation operation using the magnet.

In the agitation operation, magnetic particles 191 are dispersed in the liquid by periodically changing the direction or strength of magnetic force acting on magnetic particles 191, for example. In sample-R1 reaction tank 112, an agitation operation is performed to react magnetic particles 191, detection target substance 190a, and capture substance 192 with each other.

In FIG. 15A, sample analyzer 500 uses magnet 520 to transport magnetic particles 191 from R2 reagent tank 111 to sample-R1 reaction tank 112. Sample analyzer 500 moves magnet 520 close to cartridge 100 to transport magnetic particles 191 in an aggregated state.

In FIG. 15B, sample analyzer 500 separates magnet 520 from cartridge 100 to disperse magnetic particles 191 in sample-R1 reaction tank 112. The agitation of magnetic particles 191 is facilitated by dispersing magnetic particles 191 in sample-R1 reaction tank 112.

In FIG. 15C, sample analyzer 500 moves magnet 520 separated from cartridge 100 to agitate dispersed magnetic particles 191. Sample analyzer 500 agitates magnetic particles 191 by moving magnet 520 in the width direction or length direction of cartridge 100 or in a circular orbit about an axis parallel to the Z direction.

By periodically repeating such operations, magnetic particles 191 are dispersed in the liquid. Thus, the reaction can be efficiently progressed. In this embodiment, magnet 520 with strong magnetic force, such as a permanent magnet, is preferably used. Therefore, when cartridge 100 is close to magnet 520, magnetic particles 191 are aggregated, inhibiting efficient agitation. As in the example illustrated in FIG. 15B, the agitation of magnetic particles 191 can be facilitated by controlling the distance between cartridge 100 and magnet 520.

Figure 16A:
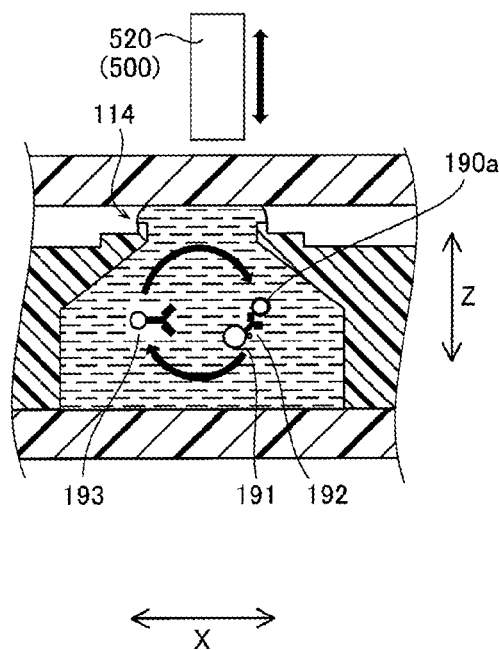
FIG. 16A and FIG. 16B are diagrams illustrating another example of the agitation operation using the magnetic force.
Figure 16B:
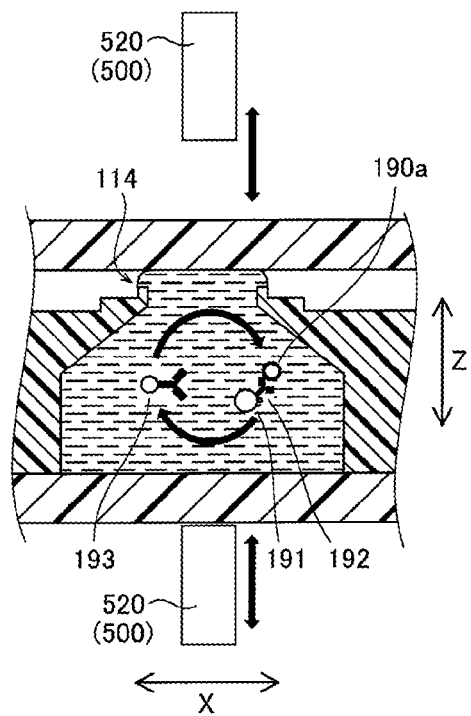

FIG. 16A and FIG. 16B illustrate another agitation example according to this embodiment.

FIG. 16A illustrates an agitation operation example in R3 reagent tank 114. Sample analyzer 500 moves magnet 520 in the Z direction in R3 reagent tank 114. By moving magnet 520 in the Z direction of cartridge 100, labeled substance 193, detection target substance 190a, magnetic particles 191, and capture substance 192 are agitated in a depth direction of R3 reagent tank 114. The agitation is facilitated entirely in the depth direction of R3 reagent tank 114 rather than agitating only in the surface of R3 reagent tank 114.

FIG. 16B illustrates another agitation operation example in R3 reagent tank 114. In the example of FIG. 16B, magnets 520 are disposed on the upper surface side and lower surface side of cartridge 100, respectively. Sample analyzer 500 moves magnets 520 on the upper surface side and lower surface side of cartridge 100 in the thickness direction of cartridge 100. In this case, the direction of the magnetic force acting on magnetic particles 191 is alternately reversed in the thickness direction of cartridge 100. The magnets 520 on the both surfaces of cartridge 100 are moved to further facilitate the agitation of the coupled body of labeled substance 193 and the magnetic particles.

(Configuration of Air Chamber)

Figure 17:
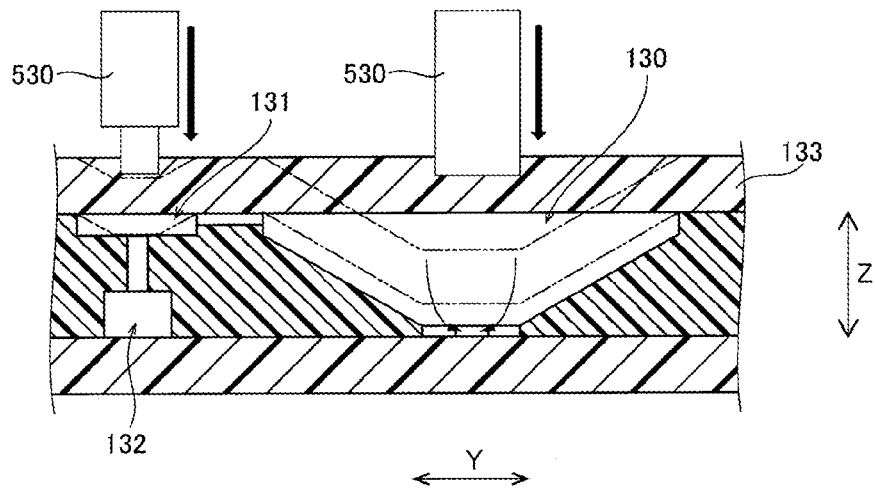
FIG. 17 is a cross-sectional view illustrating an air chamber and a valve.
Figure 18:
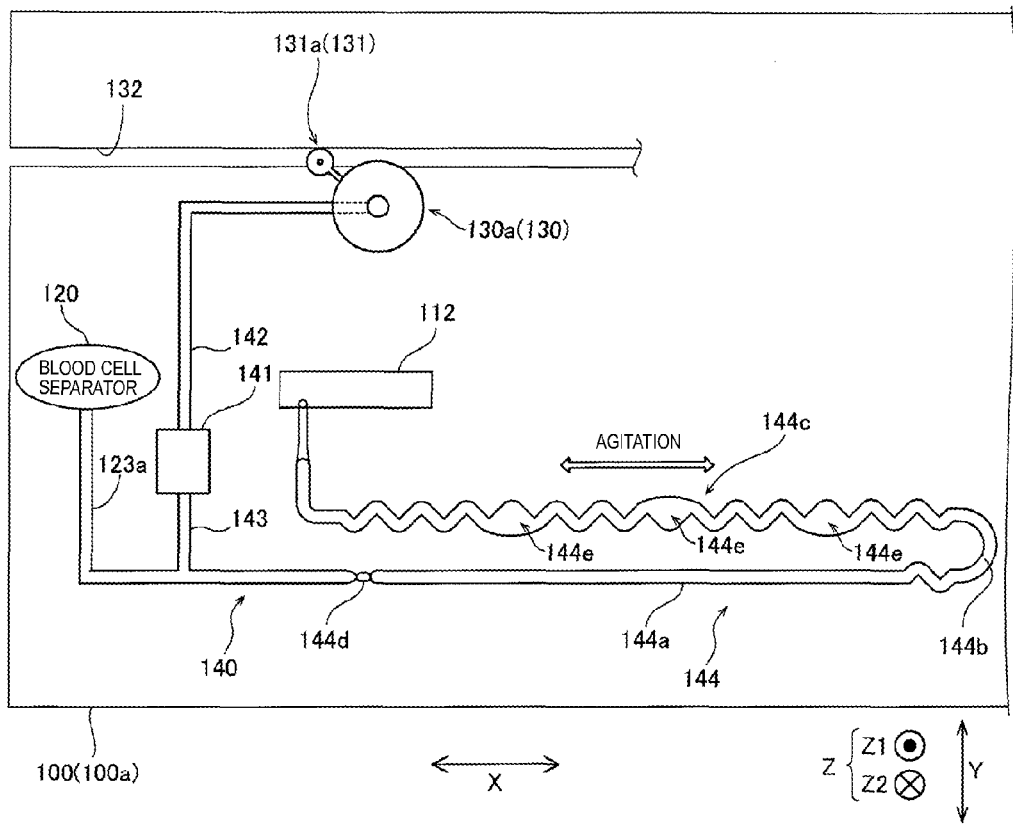
FIG. 18 is a plan view of a sample-R1 flow path.

FIGS. 17 and 18 illustrate a configuration example of air chamber 130.

Air chamber 130 is connected to valve part 131 and a portion of an air supply destination. Valve part 131 is connected to air chamber 130 and air flow path 132 connected to the outside of cartridge 100, respectively. The air outside the cartridge is taken into air chamber 130 from air flow path 132 through valve part 131.

Air chamber 130 and valve part 131 have a structure for activation by plunger 530. For example, air chamber 130 and valve part 131 are each formed into a recessed shape in the surface of cartridge main body 100a so as to have an opening in the upper part thereof, and covered with sheet 133 (see FIG. 17) that is an elastic member. Valve part 131 can close the connection portion with air flow path 132 by plunger 530 entering the inside from the outside through sheet 133. Air chamber 130 is filled with air. Air chamber 130 can discharge the internal air to the supply destination flow path by plunger 530 pushing sheet 133 into air chamber 130 from the outside.

Sample analyzer 500 discharges the air in air chamber 130 to the supply destination flow path by using plunger 530 to close valve part 131 and push sheet 133 into air chamber 130. Here, the operation of pushing sheet 133 into air chamber 130 by using plunger 530 is described as "activating air chamber 130". The operation of pushing sheet 133 into valve part 131 by using plunger 530 is described as "closing valve part 131".

In a state where valve part 131 is not closed, air chamber 130 comes into contact with the air outside the cartridge through valve part 131 and air flow path 132. When cartridge 100 is heated by heat blocks 510, the air in air chamber 130 expands. When the air in air chamber 130 expands, an increase in internal pressure of air chamber 130 causes the air to flow out to the flow path of air supply destination. As a result, the liquid in cartridge 100 may be unintentionally operated. A change in internal pressure due to the expansion of the air in air chamber 130 is suppressed by air chamber 130 coming into contact with the air outside cartridge 100 through air flow path 132. Thus, the liquid in cartridge 100 can be inhibited from being unintentionally operated.

Sample analyzer 500 may include the same number of plungers 530 as those of air chambers 130 and valve parts 131 or may include a smaller number of plunger 530 than those of air chambers 130 and valve parts 131. In such a case, air chambers 130 and valve parts 131 to be activated may be switched by moving plungers 530. The sample analyzer can be reduced in size for the reduction in the number of plungers 530.

When plunger 530 is moved, air chambers 130 or valve parts 131 can be arranged at various positions. For example, three air chambers 130 are linearly arranged in the X direction, and three valve parts 131 are linearly (see FIG. 3) arranged in the X direction. Accordingly, plunger 530 needs only be moved in the X direction. Thus, the movement mechanism can be simplified to reduce the size of the sample analyzer.

Air chamber 130a and valve part 131a illustrated in FIG. 18 are provided to transport the specimen and the R1 reagent to sample-R1 reaction tank 112. In FIG. 18, one air chamber 130a and one valve part 131a are provided. However, more than one air chamber 130a and more than one valve part 131a may be provided.

Air chamber 130a is connected to sample-R1 flow path 140. Valve part 131a is connected to air chamber 130a and air flow path 132. By closing valve part 131a and activating air chamber 130a, the specimen and R1 reagent flowing in from blood cell separator 120 can be transported to sample-R1 reaction tank 112 from sample-R1 flow path 140.

(Flow Path Structure)

Cartridge 100 has a flow path structure that facilitates mixing of liquids on a flow path.

<Sample-R1 Flow Path>

As illustrated in FIG. 18, sample-R1 flow path 140 includes, for example, R1 reagent tank 141, first portion 142, second portion 143, and mixing part 144.

R1 reagent tank 141 includes one end connected to air chamber 130a through first portion 142. R1 reagent tank 141 includes the other end connected to sample inflow path 123a through second portion 143. R1 reagent tank 141 is provided to store the R1 reagent. The R1 reagent is, for example, an antibody that can be coupled to an antigen as detection target substance 190a.

Figure 19:
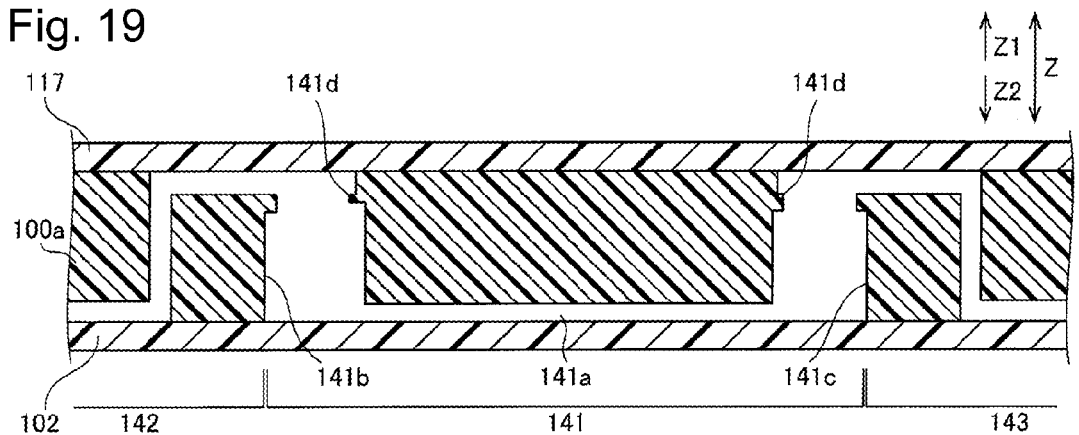
FIG. 19 is a cross-sectional view of the sample-R1 flow path.

As illustrated in FIG. 19, in the R1 reagent tank 141, reagent storage portion 141a is formed near the bottom of cartridge main body 100a in the Z direction. One side of R1 reagent tank 141 is connected to air chamber 130a through portion 141b extending in the Z direction. The other side of R1 reagent tank 141 is connected to second portion 143 through portion 141c extending in the Z direction. Portion 141b includes reduced diameter part 141d on the opposite side to the bottom of cartridge main body 100a. Portion 141c includes reduced diameter part 141d on the opposite side to the bottom of cartridge main body 100a.

Referring back to FIG. 18, mixing part 144 includes one end connected to a joint portion between second portion 143 and sample inflow path 123a connected to blood cell separator 120. Mixing part 144 includes the other end connected to sample-R1 reaction tank 112. Mixing part 144 includes straight part 144a, bent part 144b, and meander part 144c.

Straight part 144a partially overlaps with meander part 144c as seen from the short direction of cartridge 100. Straight part 144a includes narrow flow path part 144d, for example. Narrow flow path part 144d can stop the sample flowing from blood cell separator 120. In this state, the R1 reagent is sent toward the specimen from R1 reagent tank 141 by the air pressure in air chamber 130a.

Bent part 144b connects straight part 144a to meander part 144c. Bent part 144b is formed into an approximately U-shape. In a schematic view, sample-R1 flow path 140 is bent approximately 180 degrees at bent part 144b. Thus, the movement distance of the specimen can be increased, and thus the specimen can be efficiently mixed.

Meander part 144c is formed into a curved shape that enables efficient agitation of a specimen. In a planar view, for example, meander part 144c is schematically formed into a sine-wave shape. Thus, the specimen can be efficiently mixed by changing the flowing direction of the specimen.

Meander part 144c includes dilated parts 144e. Dilated parts 144e are formed by increasing the cross-sectional area of meander part 144c in a direction perpendicular to the flow path direction of the specimen. Dilated parts 144e are provided to accumulate the flow of the specimen and capture air bubbles generated in the specimen flowing through the flow path. Dilated parts 144e can further facilitate the mixing of the specimen by removing the air bubbles from the specimen flowing through meander part 144c. An arbitrary number of dilated parts 144e can be provided.

Mixing part 144 is connected to sample-R1 reaction tank 112 from the Z2 side of cartridge 100, for example. Thus, the specimen and the R1 reagent can be transported to sample-R1 reaction tank 112 from below.

<First Flow Path>

Figure 20:
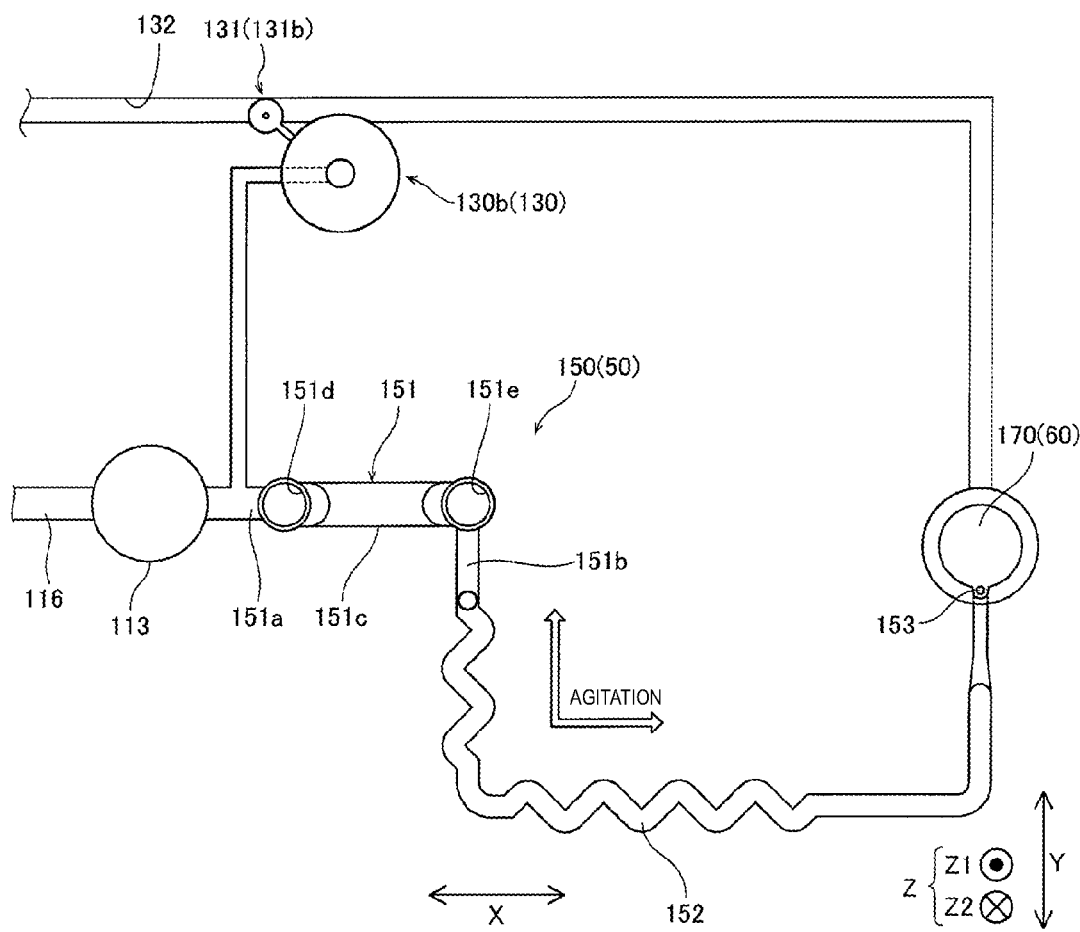
FIG. 20 is a plan view of a first flow path.

As illustrated in FIG. 20, first flow path 150 is formed in a region between passage 116 and detection tank 170, and connects passage 116 to detection tank 170. First flow path 150 includes, for example, dispersion portion 151, first portion 152, and second portion 153. First flow path 150 is provided to transport complex 190c containing detection target substance 190a, magnetic particles 191, and labeled substance 193, which is formed in R3 reagent tank 114, to the R4 reagent.

First air chamber 130b is connected to the upstream side of R4 reagent tank 151c. Valve part 131b is connected to first air chamber 130b and air flow path 132. By closing valve parts 131a and 131b and activating air chamber 130a and first air chamber 130b, mixed liquid 190m containing the R4 reagent and complex 190c can be transported to detection tank 170 through first flow path 150. First air chamber 130b has the same configuration as that of air chamber 130a, for example. Valve part 131b has the same configuration as that of valve part 131a, for example.

Mixed liquid 190m of complex 190c and the third liquid is transported through first flow path 150 by the air pressure generated in first air chamber 130b. The air pressure transports magnetic particles 191 while agitating the magnetic particles in mixed liquid 190m inside first flow path 150. Thus, magnetic particles 191 can be dispersed in mixed liquid 190m by using the air pressure. Thus, magnetic particles 191 can be sufficiently agitated.

First air chamber 130b is configured to transport magnetic particles 191 in mixed liquid 190m by the air pressure to detection tank 170 while agitating the magnetic particles in first flow path 150. Thus, magnetic particles 191 can be transported to detection tank 170 while being sufficiently agitated.

By moving mixed liquid 190m back and forth within first flow path 150 by the air pressure, magnetic particles 191 are agitated within mixed liquid 190m. Thus, the movement distance of mixed liquid 190m can be increased for more efficient agitation.

For example, by alternately deforming first air chamber 130b between an initial state and a contracted state, mixed liquid 190m is moved back and forth within first flow path 150, and magnetic particles 191 are agitated in mixed liquid 190m. Thus, the air pressure can be easily generated to efficiently agitate magnetic particles 191 within mixed liquid 190m.

First air chamber 130b can be operated by sample analyzer 500. First air chamber 130b is configured to be deformed from the initial state to the contracted state by being pushed down by plunger 530. Thus, with a simple operation using plunger 530, first air chamber 130b can be deformed, and mixed liquid 190m can be moved back and forth within first flow path 150.

The volume of first flow path 150 is larger than the volume of mixed liquid 190m. Thus, mixed liquid 190m can be easily moved back and forth in first flow path 150.

Figure 21:
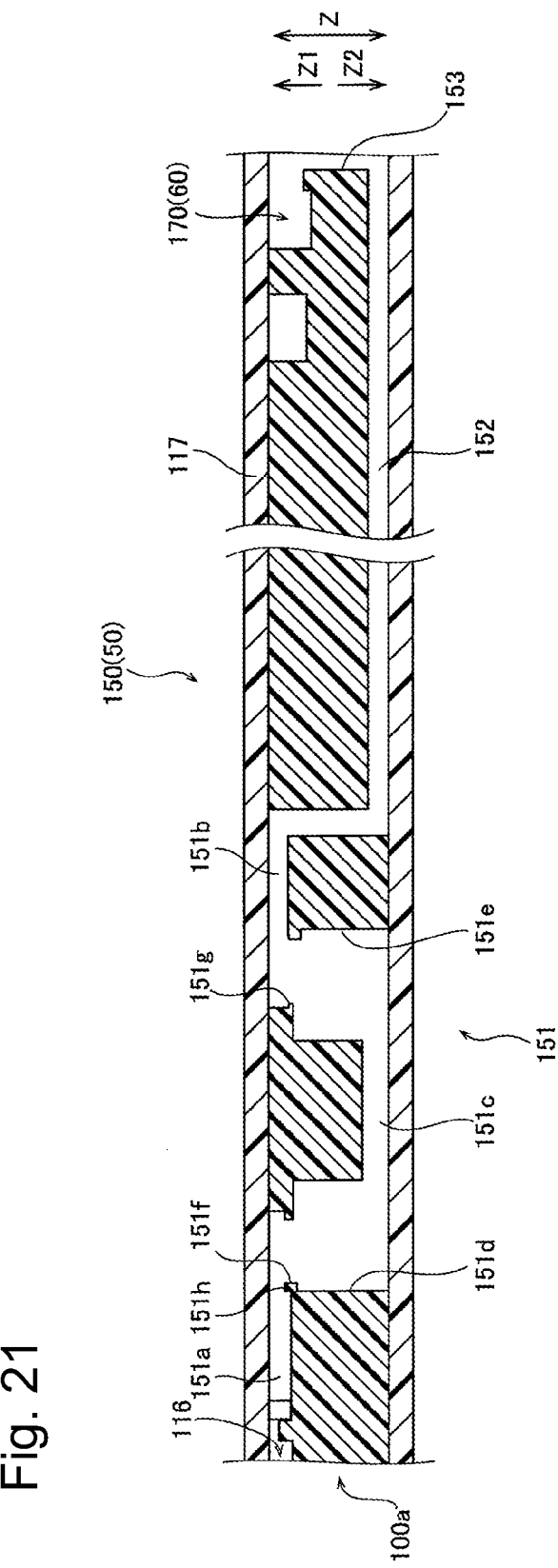
FIG. 21 is a cross-sectional view of the first flow path.

As illustrated in FIG. 21, dispersion portion 151 includes passage connection part 151a connected to passage 116 and first portion connection part 151b connected to first portion 152. Passage connection part 151a is a portion where passage 116 joins first flow path 150. Dispersion portion 151 includes R4 reagent tank 151c. R4 reagent tank 151c is formed near the bottom of cartridge main body 100a in the Z direction. R4 reagent tank 151c contains the R4 reagent, for example. The R4 reagent is a buffer solution, for example. One side of R4 reagent tank 151c is connected to passage connection part 151a through portion 151d extending in the Z direction. The other side of R4 reagent tank 151c is connected to first portion connection part 151b through portion 151e extending in the Z direction. At portion 151d, reduced diameter part 151f is formed on the opposite side to the bottom of cartridge main body 100a. At portion 151e, reduced diameter part 151g is formed on the opposite side to the bottom of cartridge main body 100a.

Step 151h is formed on reduced diameter part 151f. During sample analysis, a portion between step 151h and cover part 117 is filled with the R4 reagent.

First portion 152 is disposed at a position lower than detection tank 170 in the Z direction. First portion 152 has one end connected to dispersion portion 151 and the other end connected to second portion 153. First portion 152 is formed so as to extend in the X direction and Y direction. Thus, magnetic particles 191 can be efficiently agitated by moving the magnetic particles in the X direction and Y direction within first flow path 150 in mixed liquid 190m of complex 190c and the R4 reagent.

Second portion 153 is disposed at a position lower than detection tank 170 in the Z direction. Second portion 153 extends in the Z direction. Second portion 153 has one end connected to first portion 152 and the other end connected to detection tank 170. Second portion 153 can transport mixed liquid 190m of complex 190c and the R4 reagent to detection tank 170 from below. Thus, mixed liquid 190m of complex 190c and the R4 reagent can be inhibited from vigorously flowing in the horizontal direction in detection tank 170. As a result, mixed liquid 190m can be easily accumulated in detection tank 170.

Through first flow path 150, mixed liquid 190m can be moved both up and down in the thickness direction of cartridge 100 within the flow path. Thus, magnetic particles 191 in mixed liquid 190m can be efficiently agitated within first flow path 150.

Referring back to FIG. 20, for example, at least a portion of first flow path 150 is disposed on the extension of passage 116 in the transportation direction of magnetic particles 191 within passage 116. Thus, complex 190c containing magnetic particles 191 and labeled substance 193 can be transported to the R4 reagent without changing the transportation direction of magnetic particles 191 transported within passage 116.

First portion 152 is formed in a meandering shape, for example. As the meandering shape, a schematic sine-wave shape in a planar view can be adopted. By moving mixed liquid 190m of complex 190c and the R4 reagent in meandering first portion 152, magnetic particles 191 are agitated in mixed liquid 190m. Since meandering first portion 152 can complicate the flow of mixed liquid 190m, magnetic particles 191 can be efficiently agitated within mixed liquid 190m.

Alternatively, first flow path 150 can also be configured as follows.

Figure 22:
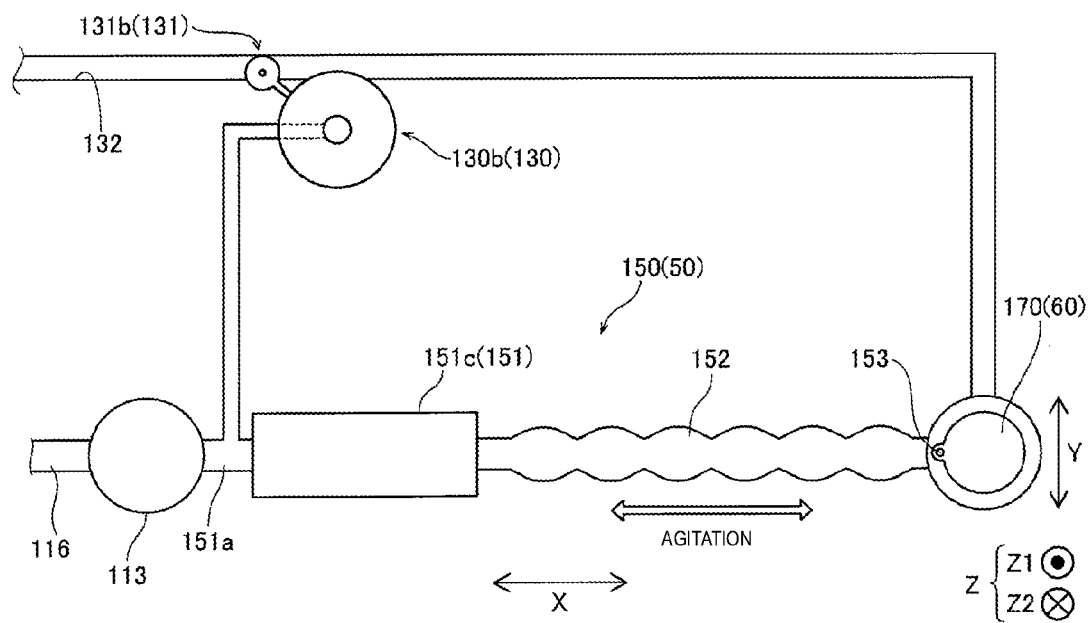
FIG. 22 is a schematic diagram of the first flow path when the cross-section perpendicular to the extending direction of the first flow path differs in the extending direction of the first flow path.

In an example illustrated in FIG. 22, first portion 152 is formed such that the cross-section perpendicular to the extending direction of first flow path 150 differs in the extending direction of first flow path 150. Thus, since the cross-sectional area of first flow path 150 can be changed according to the position, a flow rate in first flow path 150 can be easily changed. As a result, unlike the case where first flow path 150 is formed in the meandering shape, first flow path 150 can be formed in a compact size, and magnetic particle 191 in mixed liquid 190m of complex 190c and the R4 reagent can be efficiently agitated within first flow path 150.

Figure 23:
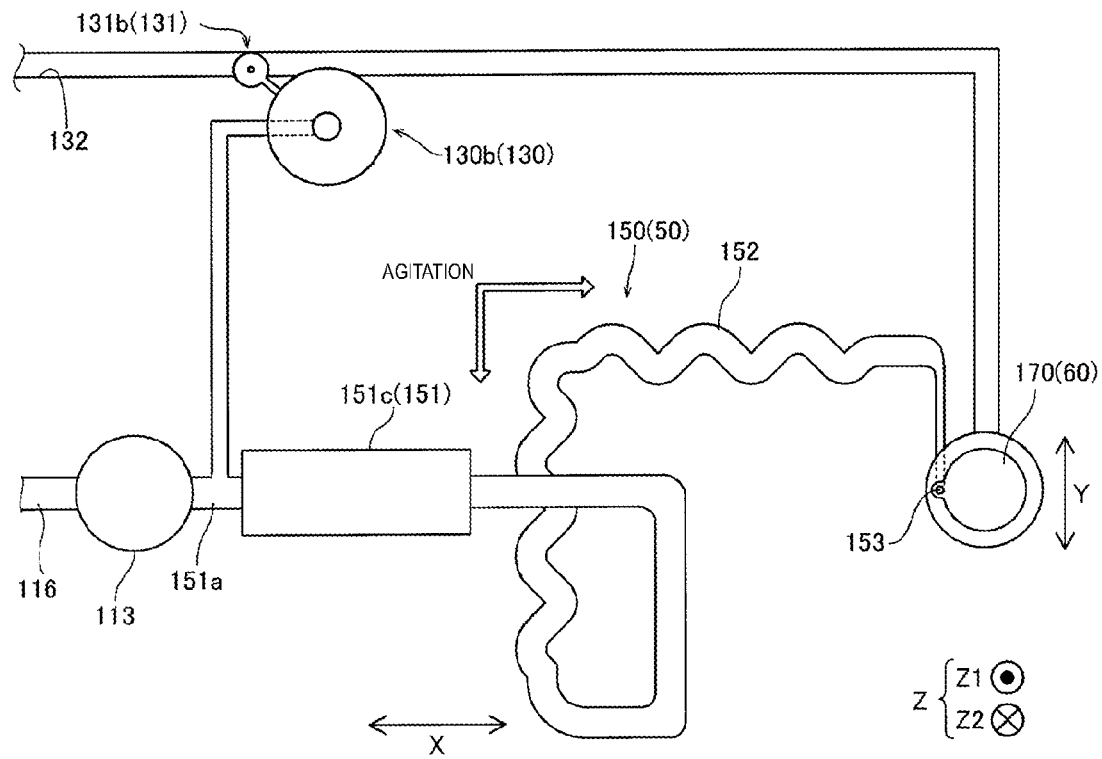
FIG. 23 is a schematic diagram of the first flow path formed into a three-dimensionally intersecting shape.

In an example illustrated in FIG. 23, first flow path 150 is formed so as to three-dimensionally intersect in a planar view, for example. First flow path 150 partially overlaps in the planar view.

Figure 24:
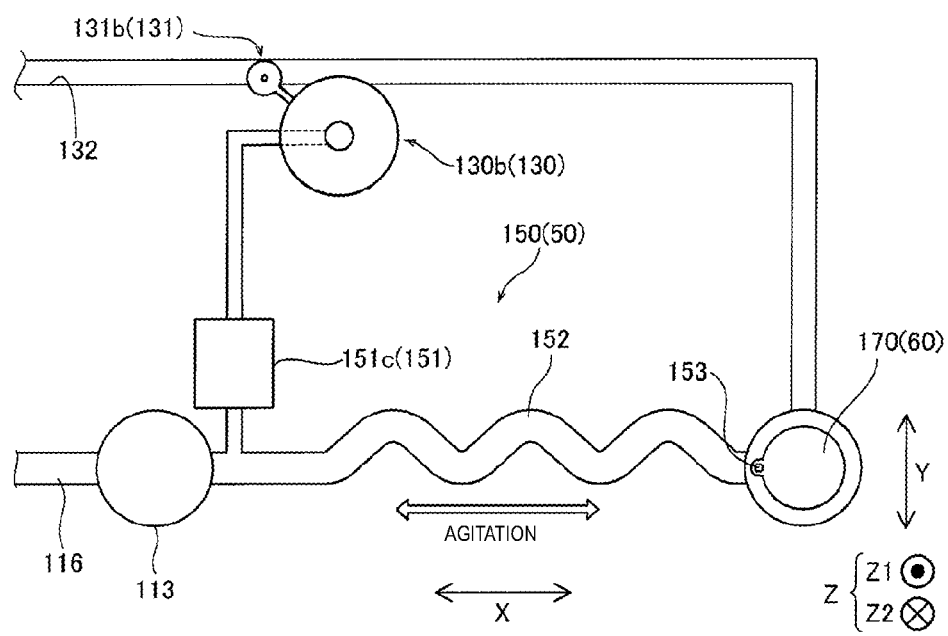
FIG. 24 is a schematic diagram illustrating another layout position of an R4 reagent tank.

In an example illustrated in FIG. 24, R4 reagent tank 151c is disposed in a flow path portion connecting first air chamber 130b to passage 116. The R4 reagent is transported to first portion 152 by the air pressure in first air chamber 130b.

Figure 25:
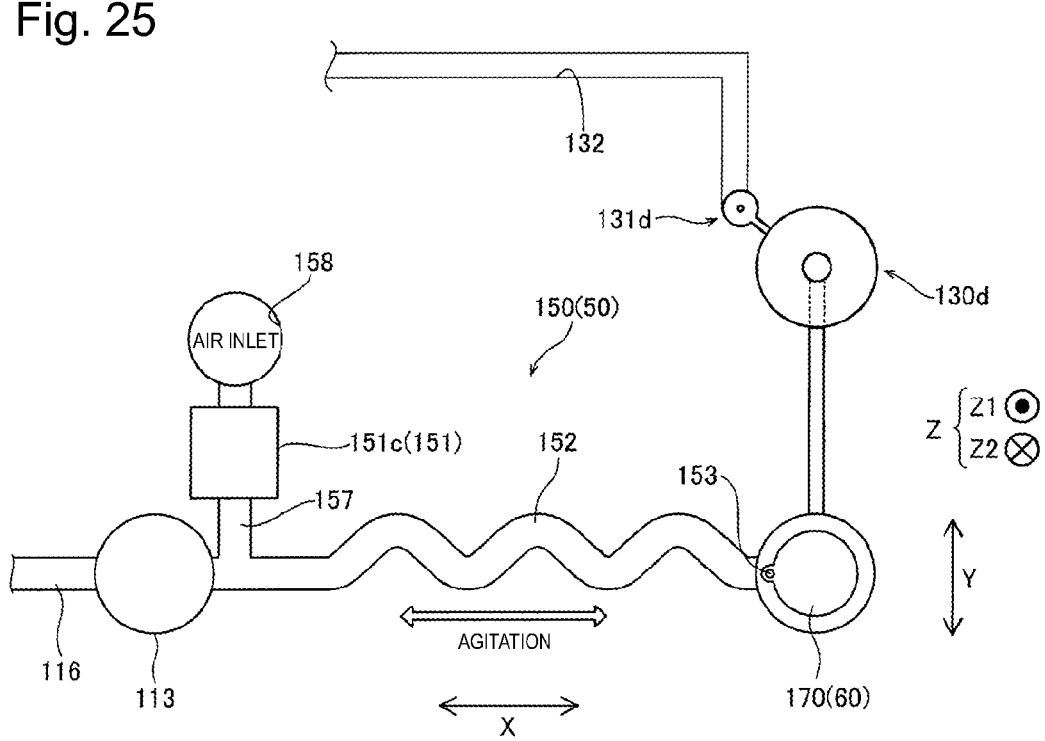
FIG. 25 is a schematic diagram illustrating an air chamber for transporting a third liquid to a dispersion portion by a negative pressure.

In an example illustrated in FIG. 25, R4 reagent tank 151c is disposed in liquid sending path 157 connected to passage 116, for example. In this case, liquid sending path 157 has air hole 158 formed on the side opposite to the side connected to passage 116. Liquid sending path 157 is connected to the outside of cartridge 100 through air hole 158. Moreover, air chamber 130d is connected to detection tank 170. Air chamber 130d is connected to air flow path 132 through valve part 131d. Air chamber 130d has the same configuration as that of air chamber 130a, for example. Valve part 131d has the same configuration as that of valve part 131a. In this example, a negative pressure generated by deforming air chamber 130d transports the R4 reagent to first portion 152. Moreover, magnetic particle 191 is agitated by the air pressure in air chamber 130d and transported to detection tank 170 in mixed liquid 190m.

Figure 26:
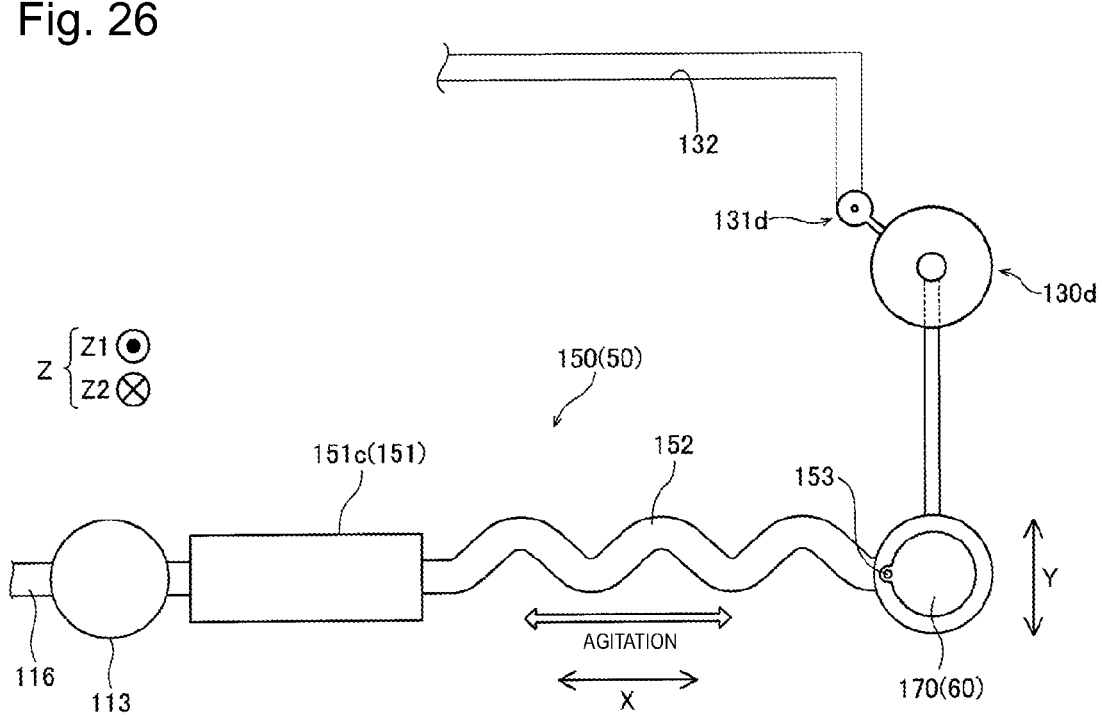
FIG. 26 is another schematic diagram illustrating an air chamber for transporting the third liquid to the dispersion portion by the negative pressure.

In an example illustrated in FIG. 26, R4 reagent tank 151c is disposed on a line connecting passage 116 and first portion 152, for example. A negative pressure generated by deforming air chamber 130d connected to detection tank 170 agitates magnetic particle 191 in mixed liquid 190m. Mixed liquid 190m is agitated by the air pressure in air chamber 130d and transported to detection tank 170.

<Second Flow Path>

Next, details of second flow path 160 are described.

Figure 27:
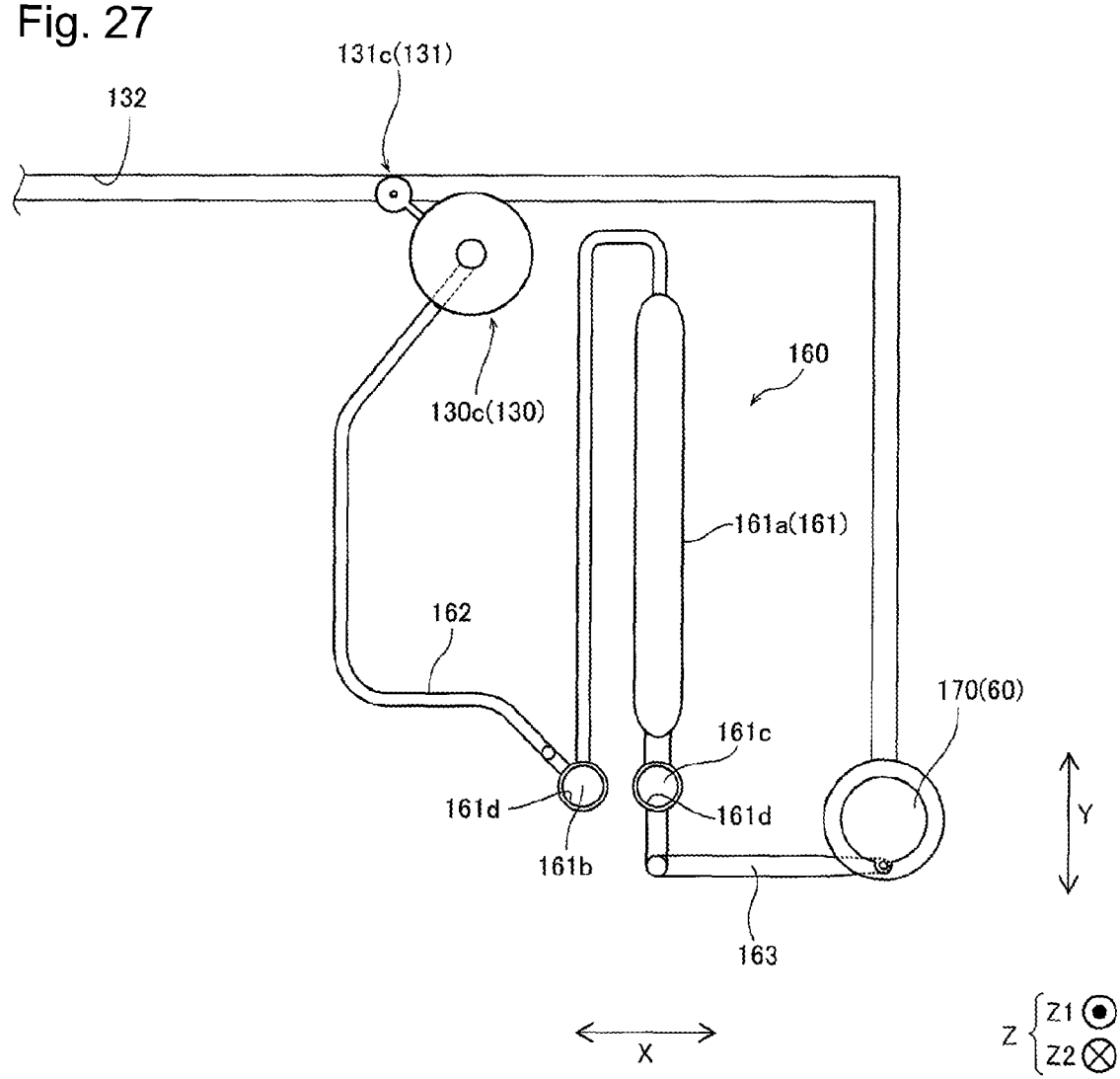
FIG. 27 is a plan view of an R5 reagent tank.

As illustrated in FIG. 27, second flow path 160 includes, for example, R5 reagent tank 161, first portion 162, and second portion 163.

R5 reagent tank 161 has one end connected to second air chamber 130c through first portion 162. R5 reagent tank 161 has the other end connected to detection tank 170 through second portion 163. R5 reagent tank 161 is provided to store a fourth reagent. The fourth reagent is, for example, the R5 reagent. The R5 reagent contains substrate 194 that facilitates light generation by reacting with complex 190c.

Second air chamber 130c is connected to second flow path 160. Valve part 131c is connected to second air chamber 130c and air flow path 132. By closing valve part 131c and activating second air chamber 130c, the R5 reagent can be transported to detection tank 170 through second flow path 160. Second air chamber 130c has the same configuration as that of air chamber 130a, for example. Valve part 131c has the same configuration as that of valve part 131a, for example.

The R5 reagent is transported to detection tank 170 by the air pressure in second air chamber 130c. Thus, the R5 reagent can be efficiently mixed with complex 190c.

R5 reagent tank 161 has basically the same configuration (see FIG. 19) as that of R1 reagent tank 141. In R5 reagent tank 161, reagent storage portion 161a is formed near the bottom of cartridge main body 100a in the Z direction, for example. One side of R5 reagent tank 161 is connected to first portion 162 through portion 161b extending in the Z direction. The other side of R5 reagent tank 161 is connected to second portion 163 through portion 161c extending in the Z direction. At portion 161b, reduced diameter part 161d is formed on the opposite side to the bottom of cartridge main body 100a. At portion 161c, reduced diameter part 161e is formed on the opposite side to the bottom of cartridge main body 100a.

Figure 28:
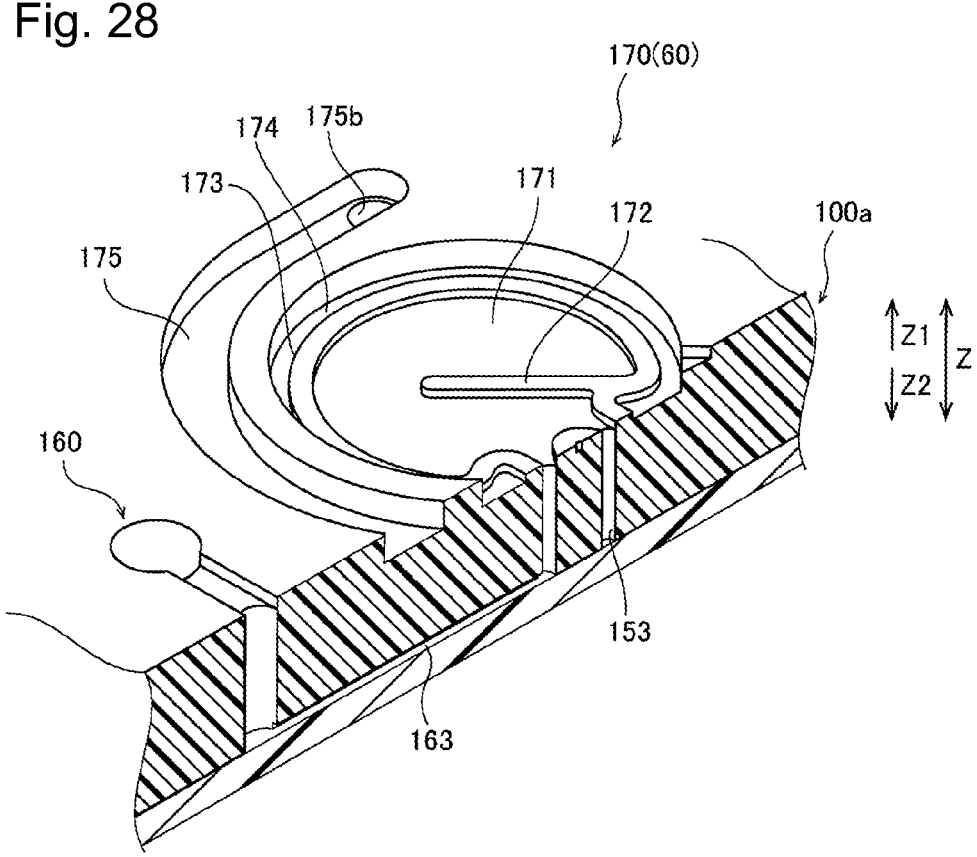
FIG. 28 is a perspective view illustrating a connection portion between the R5 reagent tank and a detection tank.

As illustrated in FIG. 28, second portion 163 is connected to detection tank 170 from the back surface side of cartridge 100, for example. Second portion 163 can transport the R5 reagent to detection tank 170 from below. Thus, the R5 reagent can be inhibited from vigorously flowing in the horizontal direction in detection tank 170. As a result, the R5 reagent can be easily accumulated in detection tank 170.

For example, second portion 163 is connected to a portion of detection tank 170 near a portion where second portion 153 of first flow path 150 is connected to detection tank 170. Thus, the R5 reagent can be efficiently mixed with mixed liquid 190m transported to detection tank 170 from first flow path 150.

(Configuration of Detection Tank)

Detection tank 170 illustrated in FIG. 28 is provided for optical measurement of mixed liquid 190m added with the R5 reagent. For example, detection tank 170 includes liquid storage part 171, flow control wall 172, step 173, external region 174, and air channel 175.

Liquid storage part 171 is formed to be concave toward the Z2 side from the Z1 side surface of cartridge main body 100a. Liquid storage part 171 is provided to accumulate mixed liquid 190m transported from first flow path 150.

Liquid storage part 171 is provided to accumulate the R5 reagent transported from second flow path 160.

Flow control wall 172 protrudes from liquid storage part 171. Flow control wall 172 is formed on the opposite side to second portion 163 of second flow path 160 with respect to second portion 153 of first flow path 150. Flow control wall 172 is tilted toward second portion 163 of second flow path 160 in a planar view. Moreover, flow control wall 172 is linearly formed in the planar view, for example.

Step 173 is formed of a portion higher than external region 174. Step 173 is disposed along the periphery of liquid storage part 171. Step 173 surrounds liquid storage part 171. Mixed liquid 190m added with the R5 reagent can be accumulated in a region inside step 173 in a planar view by the surface tension generated by step 173.

External region 174 is a region outside step 173. External region 174 is firmed into an arc shape in the planar view.

Figure 29:
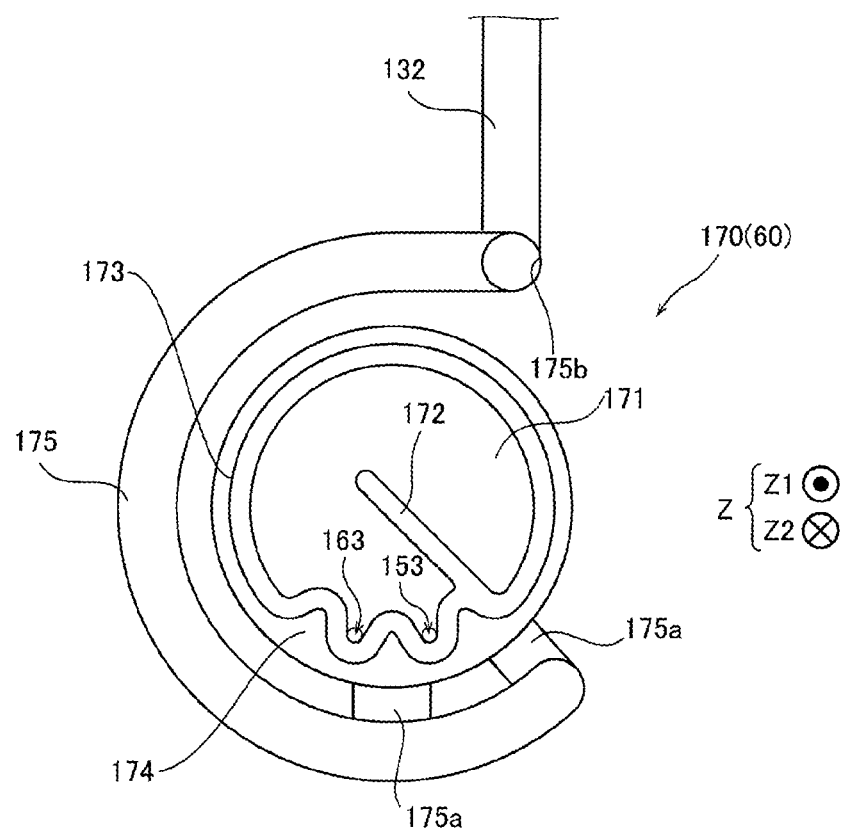
FIG. 29 is a plan view of the detection tank.

As illustrated in FIG. 29, air channel 175 is formed on the outside of external region 174. Air channel 175 is formed to be concave toward the Z2 side from the Z1 side surface of cartridge main body 100a. Air channel 175 is firmed into an arc shape in a planar view. Air channel 175 is provided with two connection parts 175a and hole part 175b.

Two connection parts 175a are provided near portions where first flow path 150 and second flow path 160 are connected to liquid storage part 171, respectively. Air channel 175 is connected to external region 174 through connection parts 175a. Air channel 175 is connected to air flow path 132 through hole part 175b.

When detection tank 170 is thus configured, the specimen accumulated in the region inside step 173 by the surface tension pushes air bubbles into air channel 175 even if the air bubbles are transported to liquid storage part 171 after mixed liquid 190m is transported to liquid storage part 171 through first flow path 150. Thus, the air bubbles can escape to the outside of cartridge 100 through air channel 175 and air flow path 132. Moreover, the air bubbles can also escape to the outside of cartridge 100 through air channel 175 and air flow path 132 when the air bubbles are transported to liquid storage part 171 after the R5 reagent is transported as the fourth regent to liquid storage part 171 through second flow path 160.

[Configurations of Respective Parts in Sample Analyzer]

Figure 30:
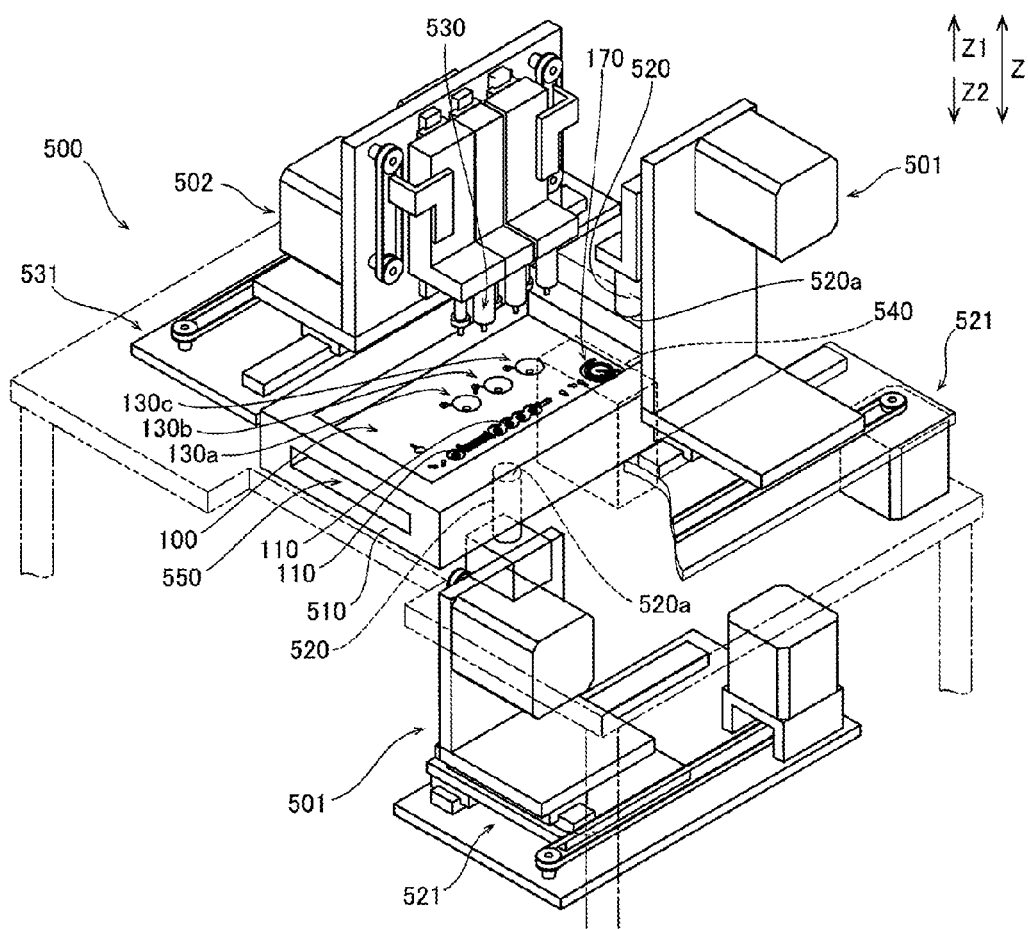
FIG. 30 is a perspective view illustrating the sample analyzer.

Configurations of the respective parts in sample analyzer 500 are described. FIG. 30 illustrates a configuration example of sample analyzer 500.

Cartridge 100 is held by heat block 510. In the configuration example of FIG. 30, magnet unit 501, plunger unit 502, and detector 540 are arranged on the sides of heat block 510. In the configuration example of FIG. 30, heat block 510 also serves as set part 550 of cartridge 100. However, heat block 510 and set part 550 may be individually provided.

Magnet unit 501 includes: magnet 520 as a magnetic source; and movement mechanism 521 configured to move magnet 520 relative to cartridge 100. Movement mechanism 521 can move magnet 520 in a horizontal direction and in a vertical direction (thickness direction of cartridge 100). When liquid containers 110 are linearly arranged, movement mechanism 521 may horizontally move only in one straight axial direction along the arrangement direction of respective liquid containers 110.

When magnets 520 are provided above and below cartridge 100, two magnet units 501 are disposed. In this case, the horizontally moving structure of movement mechanism 521 may be shared by two magnet units 501.

Plunger unit 502 includes, for example: plunger 530 that activates air chamber 130 and valve part 131; and movement mechanism 531 that moves plunger 530 relative to cartridge 100. Movement mechanism 531 can move plunger 530 in the vertical direction. When air chamber 130 and valve part 131 are linearly arranged, movement mechanism 531 may horizontally move only in one straight axial direction along the arrangement direction of air chamber 130 and valve part 131. When the same number of plungers 530 as those of air chambers 130 and valve parts 131 are provided, the horizontal positions of plungers 530 can be fixed. Thus, movement mechanism 531 may move only in the vertical direction.

Detector 540 is disposed at a position close to detection tank 170 in cartridge 100.

(Magnet)

Magnet 520 is configured to collect magnetic particles at tip 520a, for example.

(Plunger)

In the configuration example of FIG. 17, the liquid is transported by activating air chamber 130 in a closed state of valve part 131. Thus, plunger 530 for air chamber 130 and plunger 530 for valve part 131 may be configured so as to individually move up and down.

Figure 31:
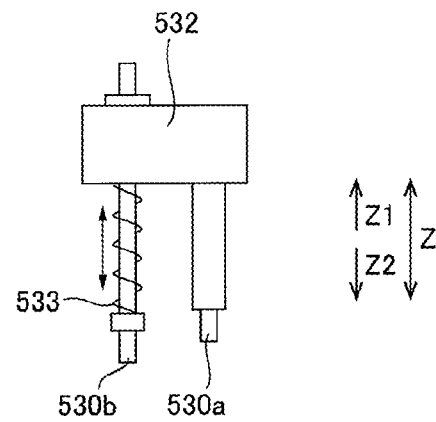
FIG. 31 is a schematic diagram illustrating a plunger unit.

In an example illustrated in FIG. 31, plunger 530a is a plunger for activating air chamber 130, and plunger 530b is a plunger for opening and closing valve part 131. Respective plungers 530a and 530b are attached to holding block 532.

Plunger 530a is fixed to holding block 532. Plunger 530b is attached to holding block 532 in a state of being movable up and down relative to holding block 532. Plunger 530b is provided with energizing member 533 that energizes plunger 530b in a direction protruding from holding block 532.

Thus, when holding block 532 is lowered toward cartridge 100, plunger 530b first closes valve part 131. When holding block 532 is further lowered in this state, energizing member 533 is compressed and plunger 530b is moved relative to holding block 532. Thus, the position of plunger 530b can be maintained even if holding block 532 is moved. Therefore, by moving holding block 532 up and down in the closed state of valve part 131, plunger 530a can move the liquid back and forth within the flow path by moving up and down relative to air chamber 130. Moreover, by further lowering holding block 532, the liquid can be sent to the portion of supply destination from the flow path.

(Temperature Control in Cartridge)

In this embodiment, sample analyzer 500 controls the temperatures of detection target substance 190a and reagent in cartridge 100 to those required in the assay. Sample analyzer 500 uses heat block 510 to control the temperatures of detection target substance 190a and reagent in cartridge 100. Heat block 510 performs the temperature control using a heating wire or the like which generates heat with unillustrated power supply, for example. When not only heating but also cooling is required, a thermoelectric element such as a Peltier element, for example, is used as heat block 510.

Figure 32:
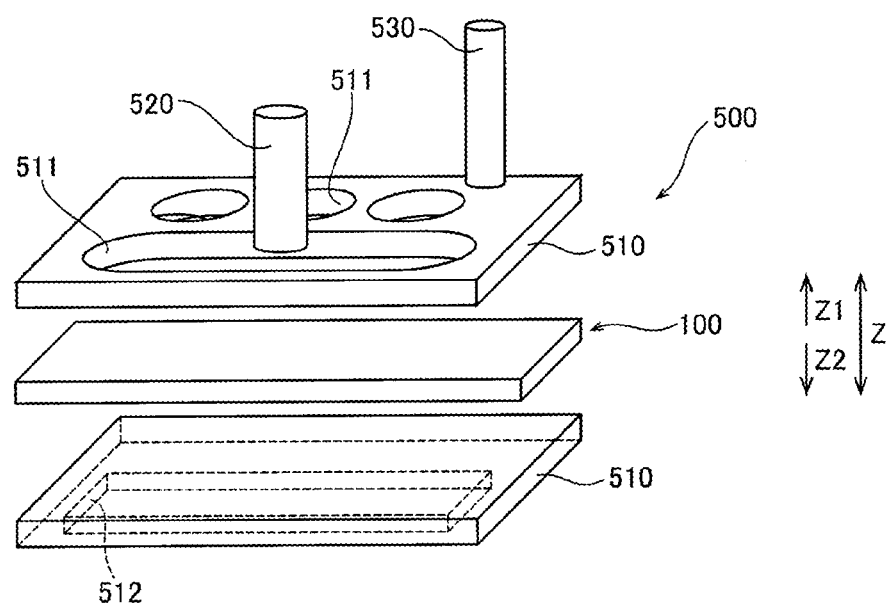
FIG. 32 is a schematic diagram illustrating heat blocks.

FIG. 32 illustrates a configuration example of the heat blocks according to this embodiment. Heat blocks 510 are disposed on the upper and lower surfaces of cartridge 100, for example. Heat block 510 may be disposed on any one of the upper and lower surfaces of cartridge 100.

Heat block 510 disposed on the lower surface of cartridge 100 is configured to cover at least a fluid structure associated with the transportation of magnetic particles 191. In this embodiment, the fluid structure associated with the transportation of magnetic particles 191 is the portion including R2 reagent tank 111, sample-R1 reaction tank 112, cleaning tank 113, R3 reagent tank 114, and passage 116 provided between liquid containers 110. Heat block 510 disposed on the lower surface of cartridge 100 may be configured to cover almost the entire lower surface of cartridge 100. By covering almost the entire lower surface of cartridge 100 with heat block 510, temperature control efficiency of cartridge 100 is improved.

Heat block 510 disposed on the upper surface of cartridge 100 has holes 511 for plunger 530 and magnet 520 to access cartridge 100. Hole 511 for plunger 530 to access cartridge 100 is provided at the position corresponding to air chamber 130 in cartridge 100. Hole 511 for magnet 520 to access cartridge 100 is extended in the longitudinal direction of cartridge 100. The hole extended in the longitudinal direction of cartridge 100 enables magnet 520 to be moved in the transportation direction of magnetic particles 191 while staying close to cartridge 100.

When magnets 520 are disposed on the upper and lower surfaces of cartridge 100, groove 512 can be provided in heat block 510 on the lower surface of cartridge 100.

Heat block 510 on the lower surface of cartridge 100 has groove 512 extending in the longitudinal direction of cartridge 100. Sample analyzer 500 applies magnetic force to cartridge 100 by inserting magnet 520 provided on the lower surface of cartridge 100 into groove 512. Groove 512 in heat block 510 does not penetrate heat block 510 from the lower surface to the upper surface. Thus, the magnetic force can be applied from the lower surface of cartridge 100 without impairing the function to control the temperature on approximately the entire lower surface of cartridge 100.

Since groove 512 is not a through-hole, the magnetic force that can be applied to cartridge 100 is assumed to be reduced. Magnet 520 on the upper surface of cartridge 100 is required to apply magnetic force having strength required to transport magnetic particles 191. On the other hand, magnet 520 provided on the lower surface of cartridge 100 contributes less to the transportation of magnetic particles 191. Thus, the magnetic force that can be applied to cartridge 100 may be relatively reduced.

In Patent Document 1, the magnetic particles coupled to the detection target substance are transported by the magnetic force to the detection tank. Here, in the case of detecting the detection target substance, by using a labeled substance with chemiluminescence assay, from a complex in which the detection target substance, the labeled substance, and the magnetic particles are coupled together, the magnetic particles are agglutinated since the complex containing the magnetic particles are transported to the detection tank by the magnetic force, which in turn causes a problem that there is an adverse effect on detection accuracy of the detection target substance in the detection tank.

The embodiments described above can suppress an adverse effect on detection accuracy of the detection target substance in the detection tank.

Note that the embodiment disclosed herein is merely illustrative in all aspects and should not be recognized as being restrictive. The scope of the invention is defined by the scope of the claims rather than by the above description of the embodiment, and is intended to include the meaning equivalent to the scope of the claims and all modifications within the scope.

The invention claimed is:

1. A sample analyzing method using a sample analysis cartridge inserted into a sample analyzer that detects a detection target substance contained in a sample, comprising:

transporting a magnetic particle supporting the detection target substance by magnetic force from a first liquid container to a second liquid container through a passage disposed between the first and second liquid containers, the first liquid container storing a first liquid containing the magnetic particle to be a support of the detection target substance, the second liquid container storing a second liquid containing a labeled substance which is to form a complex together with the detection target substance and the magnetic particle;

transporting the complex, which is formed in the second liquid container, and contains the detection target substance, the magnetic particle, and the labeled substance, to a third liquid in a flow path; and transporting the magnetic particle to a detection tank to detect the detection target substance, while agitating the magnetic particle in a mixed liquid of the complex and the third liquid within the flow path.

2. The sample analyzing method using a sample analysis cartridge according to claim 1, wherein
the magnetic particle is transported while being agitated in the mixed liquid within the flow path by an air pressure.

3. The sample analyzing method using a sample analysis cartridge according to claim 1, wherein
the magnetic particle is agitated in the mixed liquid in such a way that the mixed liquid is moved back and forth within the flow path by an air pressure.

4. The sample analyzing method using a sample analysis cartridge according claim 1, wherein
the flow path meanders, and
the magnetic particle is agitated in the mixed liquid in such a way that the mixed liquid is moved in the meandering flow path.

5. The sample analyzing method using a sample analysis cartridge according to claim 4, wherein
the mixed liquid is moved within the flow path also in a thickness direction of the sample analysis cartridge.

6. The sample analyzing method using a sample analysis cartridge according to claim 1, wherein
a fourth liquid containing a substrate that facilitates light emission by reacting with the complex is transported to the detection tank by an air pressure.

7. The sample analyzing method using a sample analysis cartridge according to claim 6, wherein
the fourth liquid is transported to a position in the detection tank near a position to which the mixed liquid is transported from the flow path.

8. A sample analysis cartridge to be inserted into a sample analyzer that detects a detection target substance contained in a sample, comprising:
a first liquid container that stores a first liquid containing a magnetic particle to be a support of the detection target substance;
a second liquid container that stores a second liquid containing a labeled substance which is to form a complex together with the detection target substance and the magnetic particle;
a passage that is disposed between the first liquid container and the second liquid container, and that transports the magnetic particle supporting the detection target substance to the second liquid container by magnetic force; and
a first flow path that transports the complex, which is formed in the second liquid container and contains the detection target substance, the magnetic particle, and the labeled substance, to a third liquid, wherein the magnetic particle is transported to a detection tank to detect the detection target substance, and the magnetic particle is configured to be agitated in a mixed liquid of the complex and the third liquid in the first flow path while being transported to the detection tank.

9. The sample analysis cartridge according to claim 8, wherein
the magnetic particle is transported while being agitated in the mixed liquid in the first flow path by an air pressure.

10. The sample analysis cartridge according to claim 8, further comprising:
an air chamber that transports the magnetic particle to the detection tank while agitating the magnetic particle in the mixed liquid in the first flow path by an air pressure.

11. The sample analysis cartridge according to claim 10, wherein
the air chamber is alternately deformed between an initial state and a contracted state, thereby moving the mixed liquid back and forth in the first flow path and agitating the magnetic particle in the mixed liquid.

12. The sample analysis cartridge according to claim 8, wherein
the first flow path is formed in a meandering shape.

13. The sample analysis cartridge according to claim 8, wherein
a volume of the first flow path is larger than a volume of the mixed liquid.

14. The sample analysis cartridge according to claim 12, wherein
the first flow path is formed to also extend in a thickness direction of the sample analysis cartridge.

15. The sample analysis cartridge according to claim 14, wherein
the first flow path includes a first portion and a second portion disposed at positions lower than the detection tank in the thickness direction,
the first portion is formed to extend in a direction perpendicular to the thickness direction, and
the second portion is formed to extend in the thickness direction and to include a first end connected to the first portion and a second end connected to the detection tank.

16. The sample analysis cartridge according to claim 8, wherein
the first flow path is disposed on an extension of the passage in a transportation direction of the magnetic particle in the passage.

17. The sample analysis cartridge according to claim 8, further comprising:
an air chamber that transports the magnetic particle to the detection tank while agitating the magnetic particle in the mixed liquid in the first flow path by an air pressure, the air chamber being a first air chamber that transports the mixed liquid to the detection tank from the first flow path; and
a second air chamber that transports a fourth liquid to the detection tank by an air pressure, the fourth liquid containing a substrate that facilitates light emission by reacting with the complex.

18. The sample analysis cartridge according to claim 17, further comprising a second flow path that is connected to the detection tank and that transports the fourth liquid to the detection tank,
wherein the second flow path is connected to a portion of the detection tank near the first flow path connected to the detection tank.

19. A sample analyzer that performs a sample analysis using a sample analysis cartridge, comprising:

a first liquid container that stores a first liquid containing a magnetic particle to be a support of a detection target substance;

a second liquid container that stores a second liquid containing a labeled substance which is to form a complex together with the detection target substance and the magnetic particle;

a passage that is disposed between the first liquid container and the second liquid container, and that transports the magnetic particle supporting the detection target substance to the second liquid container by magnetic force; and a flow path that transports the complex formed in the second liquid container, and contains the detection target substance, the magnetic particle, and the labeled substance, to a third liquid, wherein the sample analysis is performed using the sample analysis cartridge in which the magnetic particle is transported from inside of the flow path to a detection tank to detect the detection target substance, and the magnetic particle is configured to be agitated in a mixed liquid of the complex and the third liquid within the flow path while being transported to the detection tank.

20. The sample analyzer according to claim 19, wherein the sample analysis is performed using the sample analysis cartridge in which the magnetic particle is transported while being agitated in the mixed liquid within the flow path by an air pressure.

* * * * *